United States Patent
Milne et al.

(10) Patent No.: US 8,595,639 B2
(45) Date of Patent: Nov. 26, 2013

(54) VENTILATOR-INITIATED PROMPT REGARDING DETECTION OF FLUCTUATIONS IN RESISTANCE

(75) Inventors: Gary Milne, Louisville, CO (US); Kirk Hensley, Dublin, OH (US); Peter R. Doyle, Vista, CA (US); Gardner Kimm, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 164 days.

(21) Appl. No.: 12/955,523

(22) Filed: Nov. 29, 2010

(65) Prior Publication Data

US 2012/0137250 A1 May 31, 2012

(51) Int. Cl.
*G06F 3/00* (2006.01)
*A62B 7/00* (2006.01)
*G08B 23/00* (2006.01)

(52) U.S. Cl.
USPC ........ 715/771; 715/808; 715/809; 340/573.1; 340/635; 128/204.18; 128/204.23

(58) Field of Classification Search
USPC ................ 715/771, 808, 809; 340/573.1, 635
See application file for complete search history.

(56) References Cited

U.S. PATENT DOCUMENTS

| | | | |
|---|---|---|---|
| 4,546,770 A | 10/1985 | Schlessinger et al. |
| 4,752,089 A | 6/1988 | Carter |
| 4,917,080 A | 4/1990 | Bayerlein |
| 4,921,642 A | 5/1990 | LaTorraca |
| 4,954,799 A | 9/1990 | Kumar |
| 5,057,822 A | 10/1991 | Hoffman |
| 5,072,737 A | 12/1991 | Goulding |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |

(Continued)

FOREIGN PATENT DOCUMENTS

| WO | WO 95/16484 | 6/1995 |
|---|---|---|
| WO | WO9829790 | 7/1998 |

(Continued)

OTHER PUBLICATIONS

U.S. Appl. No. 12/775,550, Office Action mailed Sep. 26, 2012, 32 pgs.

(Continued)

*Primary Examiner* — Tadeese Hailu
(74) *Attorney, Agent, or Firm* — Merchant & Gould P.C.

(57) ABSTRACT

This disclosure describes systems and methods for monitoring ventilatory parameters, analyzing ventilatory data associated with those parameters, and providing useful notifications and/or recommendations to clinicians. For example, many clinicians may not easily identify or recognize data patterns and correlations indicative of a fluctuation in resistance during mechanical ventilation of a patient. Furthermore, clinicians may not easily determine potential causes for the fluctuation in resistance and/or steps for mitigating the fluctuation in resistance. According to embodiments, a ventilator may be configured to monitor and evaluate diverse ventilatory parameters to detect fluctuations in resistance and may issue suitable notifications and recommendations to the clinician based on potential causes of the fluctuation, ventilatory and/or patient data, etc. The suitable notifications and recommendations may further be provided in a hierarchical format such that the clinician may selectively access information regarding the fluctuation in resistance.

20 Claims, 8 Drawing Sheets

(56) References Cited

U.S. PATENT DOCUMENTS

| | | |
|---|---|---|
| 5,319,540 A | 6/1994 | Isaza et al. |
| 5,325,861 A | 7/1994 | Goulding |
| 5,333,606 A | 8/1994 | Schneider et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,438,980 A | 8/1995 | Phillips |
| 5,443,075 A | 8/1995 | Holscher |
| 5,490,502 A | 2/1996 | Rapoport et al. |
| 5,513,631 A | 5/1996 | McWilliams |
| 5,517,983 A | 5/1996 | Deighan et al. |
| 5,520,071 A | 5/1996 | Jones |
| 5,520,192 A | 5/1996 | Kitney et al. |
| 5,524,615 A | 6/1996 | Power |
| 5,531,221 A | 7/1996 | Power |
| 5,542,415 A | 8/1996 | Brady |
| 5,544,674 A | 8/1996 | Kelly |
| 5,549,106 A | 8/1996 | Gruenke et al. |
| 5,596,984 A | 1/1997 | O'Mahony et al. |
| 5,598,838 A | 2/1997 | Servidio et al. |
| 5,605,151 A | 2/1997 | Lynn |
| 5,630,411 A | 5/1997 | Holscher |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,678,539 A | 10/1997 | Schubert et al. |
| 5,715,415 A | 2/1998 | Dazey et al. |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,803,066 A | 9/1998 | Rapoport et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,891,023 A | 4/1999 | Lynn |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,927,274 A | 7/1999 | Servidio et al. |
| 5,931,160 A | 8/1999 | Gilmore et al. |
| 5,934,274 A | 8/1999 | Merrick et al. |
| 5,957,129 A | 9/1999 | Tham et al. |
| 5,964,220 A | 10/1999 | Boussignac et al. |
| 6,024,089 A | 2/2000 | Wallace et al. |
| 6,041,780 A | 3/2000 | Richard et al. |
| 6,047,860 A | 4/2000 | Sanders |
| 6,067,022 A | 5/2000 | Laswick et al. |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahoney et al. |
| 6,148,814 A | 11/2000 | Clemmer et al. |
| 6,158,430 A | 12/2000 | Pfeiffer et al. |
| 6,158,432 A | 12/2000 | Biondi et al. |
| 6,161,539 A | 12/2000 | Winter |
| 6,192,876 B1 | 2/2001 | Denyer et al. |
| 6,206,001 B1 | 3/2001 | Garber et al. |
| 6,206,837 B1 | 3/2001 | Brugnoli |
| 6,220,245 B1 | 4/2001 | Takabayashi et al. |
| 6,223,064 B1 | 4/2001 | Lynn et al. |
| 6,240,920 B1 | 6/2001 | Ström |
| 6,269,812 B1 | 8/2001 | Wallace et al. |
| 6,273,444 B1 | 8/2001 | Power |
| 6,283,119 B1 | 9/2001 | Bourdon |
| 6,305,372 B1 | 10/2001 | Servidio |
| 6,305,373 B1 | 10/2001 | Wallace et al. |
| 6,321,748 B1 | 11/2001 | O'Mahoney |
| 6,322,502 B1 | 11/2001 | Schoenberg et al. |
| 6,325,785 B1 | 12/2001 | Babkes et al. |
| 6,342,039 B1 | 1/2002 | Lynn et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,398,728 B1 | 6/2002 | Bardy |
| 6,412,483 B1 | 7/2002 | Jones et al. |
| 6,439,229 B1 | 8/2002 | Du et al. |
| 6,463,930 B2 | 10/2002 | Biondi et al. |
| 6,467,478 B1 | 10/2002 | Merrick et al. |
| 6,546,930 B1 | 4/2003 | Emerson et al. |
| 6,551,243 B2 | 4/2003 | Bocionek et al. |
| 6,553,991 B1 | 4/2003 | Isaza |
| 6,557,553 B1 | 5/2003 | Borrello |
| 6,564,797 B1 | 5/2003 | Mechlenburg et al. |
| 6,569,095 B2 | 5/2003 | Eggers |
| 6,571,795 B2 | 6/2003 | Bourdon |
| 6,578,575 B1 | 6/2003 | Jonson |
| 6,584,973 B1 | 7/2003 | Biondi et al. |
| 6,609,016 B1 | 8/2003 | Lynn |
| 6,622,726 B1 | 9/2003 | Du |
| 6,644,310 B1 | 11/2003 | Delache et al. |
| 6,644,312 B2 | 11/2003 | Berthon-Jones et al. |
| 6,668,824 B1 | 12/2003 | Isaza et al. |
| 6,668,829 B2 | 12/2003 | Biondi et al. |
| 6,675,801 B2 | 1/2004 | Wallace et al. |
| 6,709,405 B2 | 3/2004 | Jonson |
| 6,717,589 B1 | 4/2004 | Grillo et al. |
| 6,718,974 B1 | 4/2004 | Moberg |
| 6,718,975 B2 | 4/2004 | Blomberg |
| 6,725,447 B1 | 4/2004 | Gilman et al. |
| 6,739,337 B2 | 5/2004 | Isaza |
| 6,743,172 B1 | 6/2004 | Blike |
| 6,745,764 B2 | 6/2004 | Hickle |
| 6,748,252 B2 | 6/2004 | Lynn et al. |
| 6,752,150 B1 | 6/2004 | Remmers et al. |
| 6,760,608 B2 | 7/2004 | Lynn |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,804,656 B1 | 10/2004 | Rosenfeld et al. |
| 6,807,965 B1 | 10/2004 | Hickle |
| 6,814,074 B1 | 11/2004 | Nadjafizadeh et al. |
| 6,832,609 B2 | 12/2004 | Wright et al. |
| 6,845,773 B2 | 1/2005 | Berthon-Jones et al. |
| 6,860,266 B2 | 3/2005 | Blike |
| 6,866,040 B1 | 3/2005 | Bourdon |
| 6,949,073 B2 | 9/2005 | Sarel |
| 6,960,854 B2 | 11/2005 | Nadjafizadeh et al. |
| 6,986,347 B2 | 1/2006 | Hickle |
| 7,017,574 B2 | 3/2006 | Biondi et al. |
| 7,018,341 B2 | 3/2006 | Wright et al. |
| 7,036,504 B2 | 5/2006 | Wallace et al. |
| 7,046,254 B2 | 5/2006 | Brown et al. |

(56) References Cited

U.S. PATENT DOCUMENTS

| | | |
|---|---|---|
| 7,051,735 B2 | 5/2006 | Mechlenburg et al. |
| 7,066,173 B2 | 6/2006 | Banner et al. |
| 7,073,501 B2 | 7/2006 | Remmers et al. |
| 7,077,131 B2 | 7/2006 | Hansen |
| 7,081,091 B2 | 7/2006 | Merrett et al. |
| 7,081,095 B2 | 7/2006 | Lynn et al. |
| RE39,225 E | 8/2006 | Isaza et al. |
| 7,086,399 B2 | 8/2006 | Makinson et al. |
| 7,089,937 B2 | 8/2006 | Berthon-Jones et al. |
| 7,117,438 B2 | 10/2006 | Wallace et al. |
| 7,201,734 B2 | 4/2007 | Hickle |
| 7,207,945 B2 | 4/2007 | Bardy |
| 7,210,478 B2 | 5/2007 | Banner et al. |
| 7,222,623 B2 | 5/2007 | DeVries et al. |
| 7,247,154 B2 | 7/2007 | Hickle |
| 7,256,708 B2 | 8/2007 | Rosenfeld et al. |
| 7,258,670 B2 | 8/2007 | Bardy |
| 7,270,126 B2 | 9/2007 | Wallace et al. |
| 7,307,543 B2 | 12/2007 | Rosenfeld et al. |
| 7,308,894 B2 | 12/2007 | Hickle |
| 7,315,825 B2 | 1/2008 | Rosenfeld et al. |
| 7,321,862 B2 | 1/2008 | Rosenfeld et al. |
| 7,322,937 B2 | 1/2008 | Blomberg et al. |
| 7,334,578 B2 | 2/2008 | Biondi et al. |
| 7,346,846 B2 | 3/2008 | Rossi, Jr. et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,395,216 B2 | 7/2008 | Rosenfeld et al. |
| 7,398,115 B2 | 7/2008 | Lynn |
| 7,428,902 B2 | 9/2008 | Du et al. |
| 7,433,827 B2 | 10/2008 | Rosenfeld et al. |
| 7,454,359 B2 | 11/2008 | Rosenfeld et al. |
| 7,454,360 B2 | 11/2008 | Rosenfeld et al. |
| 7,460,959 B2 | 12/2008 | Jafari |
| 7,467,094 B2 | 12/2008 | Rosenfeld et al. |
| 7,475,019 B2 | 1/2009 | Rosenfeld et al. |
| 7,487,773 B2 | 2/2009 | Li |
| 7,520,279 B2 | 4/2009 | Berthon-Jones |
| 7,556,038 B2 | 7/2009 | Kirby et al. |
| 7,561,912 B2 | 7/2009 | Schatz et al. |
| 7,562,657 B2 | 7/2009 | Blanch et al. |
| 7,565,905 B2 | 7/2009 | Hickle |
| 7,650,291 B2 | 1/2010 | Rosenfeld et al. |
| 7,654,802 B2 | 2/2010 | Crawford, Jr. et al. |
| 7,681,571 B2 | 3/2010 | Makinson et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,778,851 B2 | 8/2010 | Schoenberg et al. |
| 7,784,461 B2 | 8/2010 | Figueiredo et al. |
| 7,802,571 B2 | 9/2010 | Tehrani |
| 7,823,588 B2 | 11/2010 | Hansen |
| 7,831,450 B2 | 11/2010 | Schoenberg et al. |
| 7,855,716 B2 | 12/2010 | McCreary et al. |
| D632,796 S | 2/2011 | Ross et al. |
| D632,797 S | 2/2011 | Ross et al. |
| 7,886,231 B2 | 2/2011 | Hopermann |
| 7,886,739 B2 | 2/2011 | Soliman |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,224,636 B2 | 7/2012 | Kundert |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0004893 A1 | 6/2001 | Biondi et al. |
| 2001/0027791 A1 | 10/2001 | Wallace et al. |
| 2002/0023644 A1 | 2/2002 | Berthon-Jones |
| 2002/0026941 A1 | 3/2002 | Biondi et al. |
| 2002/0117173 A1 | 8/2002 | Lynn et al. |
| 2002/0177758 A1 | 11/2002 | Schoenberg et al. |
| 2003/0036687 A1 | 2/2003 | Schoenberg et al. |
| 2003/0106553 A1 | 6/2003 | Vanderveen |
| 2003/0121519 A1 | 7/2003 | Estes et al. |
| 2003/0140928 A1 | 7/2003 | Bui et al. |
| 2003/0141981 A1 | 7/2003 | Bui et al. |
| 2003/0153818 A1 | 8/2003 | Bocionek et al. |
| 2003/0158466 A1 | 8/2003 | Lynn et al. |
| 2003/0188748 A1 | 10/2003 | Sinderby et al. |
| 2003/0230308 A1 | 12/2003 | Linden |
| 2004/0041828 A1 | 3/2004 | Zellhoefer |
| 2004/0121767 A1 | 6/2004 | Simpson et al. |
| 2004/0167804 A1 | 8/2004 | Simpson et al. |
| 2004/0172302 A1 | 9/2004 | Martucci et al. |
| 2004/0236240 A1 | 11/2004 | Kraus et al. |
| 2004/0244807 A1 | 12/2004 | Sun et al. |
| 2005/0016534 A1 | 1/2005 | Ost |
| 2005/0039127 A1 | 2/2005 | Davis |
| 2005/0039748 A1 | 2/2005 | Andrieux |
| 2005/0043969 A1 | 2/2005 | Sarel |
| 2005/0055242 A1 | 3/2005 | Bello et al. |
| 2005/0065817 A1 | 3/2005 | Mihai et al. |
| 2005/0112325 A1 | 5/2005 | Hickle |
| 2005/0124866 A1 | 6/2005 | Elaz et al. |
| 2005/0133024 A1 | 6/2005 | Coifman |
| 2005/0139212 A1 | 6/2005 | Bourdon |
| 2005/0188991 A1 | 9/2005 | Sun et al. |
| 2005/0204310 A1 | 9/2005 | De Zwart et al. |
| 2006/0085229 A9 | 4/2006 | Rosenfeld et al. |
| 2006/0089543 A1 | 4/2006 | Kim et al. |
| 2006/0112959 A1 | 6/2006 | Mechlenburg et al. |
| 2006/0122869 A9 | 6/2006 | Rosenfeld et al. |
| 2006/0135878 A1 | 6/2006 | Wright et al. |
| 2006/0144144 A1 | 7/2006 | Seto |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0161459 A9 | 7/2006 | Rosenfeld et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0201506 A1 | 9/2006 | Makinson et al. |
| 2006/0235324 A1 | 10/2006 | Lynn |
| 2006/0237015 A1 | 10/2006 | Berthon-Jones et al. |
| 2006/0249149 A1 | 11/2006 | Meier et al. |
| 2006/0249151 A1 | 11/2006 | Gambone |
| 2006/0271409 A1 | 11/2006 | Rosenfeld et al. |
| 2006/0276701 A1 | 12/2006 | Ray |
| 2006/0294464 A1 | 12/2006 | Tokimoto et al. |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0050715 A1 | 3/2007 | Behar |
| 2007/0077200 A1 | 4/2007 | Baker |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0163579 A1 | 7/2007 | Li et al. |
| 2007/0173702 A1 | 7/2007 | Dlugos et al. |
| 2007/0191688 A1 | 8/2007 | Lynn |

(56) References Cited

U.S. PATENT DOCUMENTS

| | | |
|---|---|---|
| 2007/0191697 A1 | 8/2007 | Lynn et al. |
| 2007/0199566 A1 | 8/2007 | Be'eri |
| 2007/0203415 A1 | 8/2007 | Bardy |
| 2007/0203422 A1 | 8/2007 | Bardy |
| 2007/0203423 A1 | 8/2007 | Bardy |
| 2007/0213658 A1 | 9/2007 | Hickle |
| 2007/0227537 A1 | 10/2007 | Bemister et al. |
| 2007/0232867 A1 | 10/2007 | Hansmann |
| 2007/0284361 A1 | 12/2007 | Nadjafizadeh et al. |
| 2008/0000479 A1 | 1/2008 | Elaz et al. |
| 2008/0021379 A1 | 1/2008 | Hickle |
| 2008/0041380 A1 | 2/2008 | Wallace et al. |
| 2008/0053441 A1 | 3/2008 | Gottlib et al. |
| 2008/0066752 A1 | 3/2008 | Baker et al. |
| 2008/0072896 A1 | 3/2008 | Setzer et al. |
| 2008/0072900 A1 | 3/2008 | Kenyon et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0086691 A1 | 4/2008 | Hopermann |
| 2008/0091117 A1 | 4/2008 | Choncholas et al. |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0200775 A1 | 8/2008 | Lynn |
| 2008/0200819 A1 | 8/2008 | Lynn et al. |
| 2008/0236582 A1 | 10/2008 | Tehrani |
| 2008/0314385 A1 | 12/2008 | Brunner et al. |
| 2009/0020120 A1 | 1/2009 | Schatzl et al. |
| 2009/0143694 A1 | 6/2009 | Krauss et al. |
| 2009/0149723 A1 | 6/2009 | Krauss et al. |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1* | 10/2009 | Baker et al. ............... 128/204.23 |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0270752 A1 | 10/2009 | Coifman |
| 2009/0275811 A1 | 11/2009 | Schatz et al. |
| 2009/0293877 A1 | 12/2009 | Blanch et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0314290 A1 | 12/2009 | Hickle |
| 2010/0011307 A1 | 1/2010 | Desfossez et al. |
| 2010/0024820 A1 | 2/2010 | Bourdon |
| 2010/0030091 A1 | 2/2010 | Fine |
| 2010/0037895 A1 | 2/2010 | Berthon-Jones et al. |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0108064 A1 | 5/2010 | Blackwell et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0192094 A1 | 7/2010 | Jeha et al. |
| 2010/0199015 A1 | 8/2010 | Martucci et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |
| 2010/0292544 A1 | 11/2010 | Sherman et al. |
| 2010/0300446 A1 | 12/2010 | Nicolazzi et al. |
| 2011/0004489 A1 | 1/2011 | Schoenberg et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1* | 6/2011 | Skidmore et al. ............. 715/800 |
| 2011/0146681 A1 | 6/2011 | Jafari et al. |
| 2011/0146683 A1 | 6/2011 | Jafari et al. |
| 2011/0154241 A1* | 6/2011 | Skidmore et al. ............. 715/771 |
| 2011/0168177 A1 | 7/2011 | Connor |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1* | 2/2012 | Skidmore ..................... 715/777 |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |

(56) References Cited

U.S. PATENT DOCUMENTS

| | | |
|---|---|---|
| 2012/0216811 A1 | 8/2012 | Kimm et al. |
| 2012/0226444 A1 | 9/2012 | Milne et al. |
| 2012/0247471 A1 | 10/2012 | Masic et al. |

FOREIGN PATENT DOCUMENTS

| | | |
|---|---|---|
| WO | WO 98/41267 | 9/1998 |
| WO | WO 98/41269 | 9/1998 |
| WO | WO 98/41270 | 9/1998 |
| WO | WO 98/41271 | 9/1998 |
| WO | WO9853732 | 12/1998 |
| WO | WO 99/62403 | 12/1999 |
| WO | WO 00/45882 | 8/2000 |
| WO | WO0079466 | 12/2000 |
| WO | WO 01/00264 | 1/2001 |
| WO | WO 01/00265 | 1/2001 |
| WO | WO 02/45566 | 6/2002 |
| WO | WO 02/058619 | 8/2002 |
| WO | WO 02/095200 | 11/2002 |
| WO | WO 03/053503 | 7/2003 |
| WO | WO 03/102850 | 12/2003 |
| WO | WO 2004/030509 | 4/2004 |
| WO | WO 2004/069095 | 8/2004 |
| WO | WO 2004/070546 | 8/2004 |
| WO | WO 2004/070548 | 8/2004 |
| WO | WO 2004/070549 | 8/2004 |
| WO | WO 2004/070556 | 8/2004 |
| WO | WO 2004/070557 | 8/2004 |
| WO | WO 2004/070562 | 8/2004 |
| WO | WO 2004/070994 | 8/2004 |
| WO | WO 2004/070995 | 8/2004 |
| WO | WO 2004/082751 | 9/2004 |
| WO | WO 2005/050525 | 6/2005 |
| WO | WO 2005/051177 | 6/2005 |
| WO | WO 2006/012205 | 2/2006 |
| WO | WO 2007/050435 | 5/2007 |
| WO | WO 2007/85110 | 8/2007 |
| WO | WO 2007/131314 | 11/2007 |
| WO | WO2007145948 | 12/2007 |
| WO | WO 2008/021222 | 2/2008 |
| WO | WO 2009/149351 | 12/2009 |
| WO | WO 2010/011928 | 1/2010 |
| WO | WO 2011/139586 | 11/2011 |

OTHER PUBLICATIONS

U.S. Appl. No. 12/775,565, Office Action mailed Oct. 30, 2012, 11 pgs.

U.S. Appl. No. 12/826,828, Office Action mailed Nov. 2, 2012, 17 pgs.

U.S. Appl. No. 12/826,847, Office Action mailed Nov. 2, 2012, 16 pgs.

U.S. Appl. No. 12/827,075, Office Action mailed Nov. 9, 2012, 16 pgs.

U.S. Appl. No. 12/827,130, Office Action mailed Nov. 9, 2012, 16 pgs.

Puritan Bennett 840 Ventilator System Smarter Breath Delivery information sheet by tyco Healthcare, undated, 1 page.

Tobin, M. "Principles and Practices of Mechanical Ventilation," Second Ed. McGraw Hill 2006. p. 1062.

Thille, A., et al. "Patient-Ventilator Asynchrony During Assisted Mechanical Ventilation," Intensive Care Med. (2006) 32:1515-1522.

The ARDSNET. "Ventilation with Lower Tidal Volumes as Compared with Traditional Tidal Volumes For Acute Lung Injury and the Acute Respiratory Distress Syndrome," New England Journal of Medicine, vol. 342 No. 18, May 4, 2000, pp. 1301-1308.

7200 Series Ventilator, Options, and Accessories: Operators Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1988, pp. 1-32.

800 Operators and Technical Reference Manual. Series Ventilator System, Nellcor Puritan Bennett, Part No. 4-070088-00, Rev. L, Aug. 2010, pp. 1-476.

840 Operators and Technical Reference Manual. Ventilator System, Nellcor Puritan Bennett, Part No. 4-075609-00, Rev. G, Oct. 2006, pp. 1-424.

Egan's Fundamentals of Respiratory Care (2003) $8^{th}$ Edition, Editors Robert L. Wilkins, James K. Stoller and Craig L. Scanlan, p. 996.

Mechanical Ventilation: Physiological and Clinical Applications (2006) $4^{th}$ Edition, Editors Susan P. Pilbeam and J.M. Cairo, pp. 46-47, 144, 158-160, 168-171, 178-181, 195-202, 222-225, 373-376.

PCT International Search Report and Written Opinion mailed Feb. 23, 2012; International Application No. PCT/US2011/062301, 11 pgs.

Sassoon, Catherine, MD., "Triggering of the Ventilator in Patient-Ventilator Interactions", Respiratory Care, Jan. 2011, vol. 56, No. 1, pgs. 39-51.

U.S. Appl. No. 12/775,550, Advisory Action mailed Apr. 12, 2013, 3 pgs.

U.S. Appl. No. 12/775,565, Advisory Action mailed Apr. 9, 2013, 3 pgs.

U.S. Appl. No. 12/827,130, Office Action mailed May 8, 2013, 15 pgs.

U.S. Appl. No. 12/827,075, Office Action mailed Apr. 23, 2013, 17 pgs.

U.S. Appl. No. 12/826,847, Office Action mailed Apr. 24, 2013, 14 pgs.

U.S. Appl. No. 12/826,828, Office Action mailed Apr. 24, 2013, 15 pgs.

U.S. Appl. No. 12/955,422, Office Action mailed Apr. 23, 2013, 27 pgs.

U.S. Appl. No. 13/035,974, Office Action mailed Mar. 29, 2013, 14 pgs.

U.S. Appl. No. 12/775,550, Office Action mailed Feb. 14, 2013, 32 pgs.

U.S. Appl. No. 12/775,565, Office Action mailed Feb. 14, 2013, 10 pgs.

U.S. Appl. No. 12/775,565, Office Action mailed Jun. 13, 2013, 8 pgs.

U.S. Appl. No. 12/775,550, Office Action mailed Jul. 18, 2013, 37 pgs.

U.S. Appl. No. 12/775,565, Notice of Allowance mailed Sep. 18, 2013, 6 pgs.

U.S. Appl. No. 12/826,828, Notice of Allowance mailed Aug. 6, 2013, 4 pgs.

U.S. Appl. No. 12/826,847, Notice of Allowance mailed Aug. 5, 2013, 3 pgs.

U.S. Appl. No. 12/827,075, Notice of Allowance mailed Aug. 6, 2013, 3 pgs.

U.S. Appl. No. 12/827,130, Notice of Allowance mailed Aug. 8, 2013, 4 pgs.

U.S. Appl. No. 12/903,358, Office Action mailed Aug. 19, 2013, 15 pgs.

U.S. Appl. No. 12/955,368, Office Action mailed Aug. 2, 2013, 12 pgs.

U.S. Appl. No. 13/035,974, Office Action mailed Sep. 23, 2013, 14 pgs.

* cited by examiner

VENTILATOR-INITIATED PROMPT REGARDING DETECTION OF FLUCTUATIONS IN RESISTANCE

INTRODUCTION

A ventilator is a device that mechanically helps patients breathe by replacing some or all of the muscular effort required to inflate and deflate the lungs. In recent years, there has been an accelerated trend towards an integrated clinical environment. That is, medical devices are becoming increasingly integrated with communication, computing, and control technologies. As a result, modern ventilatory equipment has become increasingly complex, providing for detection, monitoring, and evaluation of a myriad of ventilatory parameters during ventilation of a patient. However, due to the shear magnitude of available ventilatory data, many clinicians may not readily assess and evaluate the available data to detect certain patient conditions and/or changes in patient condition.

Specifically, fluctuations in resistance may be indicative of a number of disparate patient and/or ventilator conditions. The location of a change in resistance may be an important factor in determining the cause for the change. However, this may be difficult for a clinician to determine as resistance may arise in the patient airway, the artificial airway (endotracheal or tracheostomy tube), the inspiratory limb or the expiratory limb of the ventilatory circuit, the expiratory filter, etc. For example, an increase in resistance may be detrimental to patient condition due to an increase in the work of breathing (WOB) and may lead to other adverse consequences such as Auto-PEEP. Furthermore, an increase in resistance may be the result of a variety of diverse causes including, inter alia, mucous buildup in the artificial airway, a kink or obstruction in the ventilatory circuit, an obstructed expiratory filter, changing lung conditions, poor patient position, etc. In contrast, a decrease in resistance may be indicative of changing lung conditions, a leak in the ventilatory circuit, improved patient position, etc. Fluctuations in resistance are difficult to detect because resistance is generally not measured directly, but may be implicated by slight changes in a variety of different parameters. Furthermore, due to the variety of potential causes, fluctuations in resistance may be difficult for a clinician to efficiently and effectively address during the ventilation of a patient.

Ventilator-Initiated Prompt Regarding Detection of Fluctuation in Resistance

This disclosure describes systems and methods for monitoring and evaluating ventilatory parameters, analyzing ventilatory data associated with those parameters, and providing useful notifications and/or recommendations to clinicians. Modern ventilators monitor, evaluate, and graphically represent a myriad of ventilatory parameters. However, many clinicians may not easily identify or recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect or recognize fluctuations in resistance during mechanical ventilation of a patient. According to embodiments, a ventilator may be configured to monitor and evaluate diverse ventilatory parameters to detect fluctuations in resistance and may issue suitable notifications and recommendations to the clinician depending on potential causes of the fluctuation, the magnitude of the fluctuation, ventilatory and/or patient data, etc. The suitable notifications and recommendations may further be provided in a hierarchical format such that the clinician may selectively access summarized and/or detailed information regarding the fluctuation in resistance. In more automated systems, recommendations may be automatically implemented to mitigate the detected fluctuation in resistance.

According to embodiments, a ventilator-implemented method is provided for issuing a prompt in response to detecting a fluctuation in resistance during ventilation of a patient. The method comprises retrieving ventilatory data and identifying a maximum threshold and a minimum threshold for resistance. Further, the method comprises trending resistance during ventilation of the patient and detecting a fluctuation in resistance when the trended resistance breaches one of the maximum threshold and the minimum threshold. Upon detection of the fluctuation in resistance, the method includes displaying a notification.

According to additional embodiments, a ventilatory system for issuing a prompt in response to detecting a fluctuation in resistance during ventilation of a patient is provided. The ventilatory system performs a method that comprises retrieving ventilatory data and identifying a maximum threshold and a minimum threshold for resistance. Further, the method comprises trending resistance during ventilation of the patient and detecting a fluctuation in resistance when the trended resistance breaches one of the maximum threshold and the minimum threshold. Upon detection of the fluctuation in resistance, the method includes displaying a notification.

According to additional embodiments, a ventilator processing interface for displaying one or more prompts in response to detecting a fluctuation in resistance is provided. The ventilator processing interface comprises a means for retrieving at least some ventilatory data, a means for determining the fluctuation in resistance, and means for displaying a prompt comprising a notification of the fluctuation in resistance.

According to additional embodiments, a graphical user interface for displaying one or more prompts in response to detecting a fluctuation in resistance is provided. The graphical user interface comprising at least one window, the at least one window having one or more elements comprising at least one prompt element for communicating information regarding detection of a fluctuation in resistance. For example, the at least one prompt element displays a notification regarding the fluctuation in resistance.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the claims.

BRIEF DESCRIPTION OF THE DRAWINGS

The following drawing figures, which form a part of this application, are illustrative of described technology and are not meant to limit the scope of the claims in any manner, which scope shall be based on the claims appended hereto.

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment for alerting and advising clinicians regarding change in patient condition.

According to embodiments, the ventilator may be configured to collect ventilatory data by Monitoring and evaluating diverse ventilatory parameters and/or patient physiological data. Based on the ventilatory data, the ventilator may issue suitable notifications and recommendations to the clinician upon detecting a fluctuation in resistance. That is, the ventilator may detect an increase or a decrease in resistance based on, inter alia, ventilatory data (e.g., flow, volume, pressure, compliance, ventilator setup data, etc.), patient data (e.g., a patient body weight, a patient diagnosis, a patient gender, a patient age, etc.) and/or any suitable protocol, equation, etc. The ventilator may also detect an increase or a decrease in resistance at a particular location within the ventilatory system, e.g., expiratory limb, patient airway, etc. Furthermore, the ventilator may detect one or more projected causes of the increase or the decrease in resistance (e.g., clogged expiratory filter, leak in the ventilatory circuit, condensate accumulation in the ventilatory circuit, mucous plugging of the patient airway, etc.) based on whether an increase or decrease in resistance was detected, a location of the increase or decrease, patient data, etc. Based on the one or more projected causes of the fluctuation, the ventilator may be configured to provide a notification and/or one or more recommendations for mitigating the detected fluctuation in resistance.

These and other embodiments will be discussed in further detail with reference to the following figures.

Ventilator System

Figure 1:
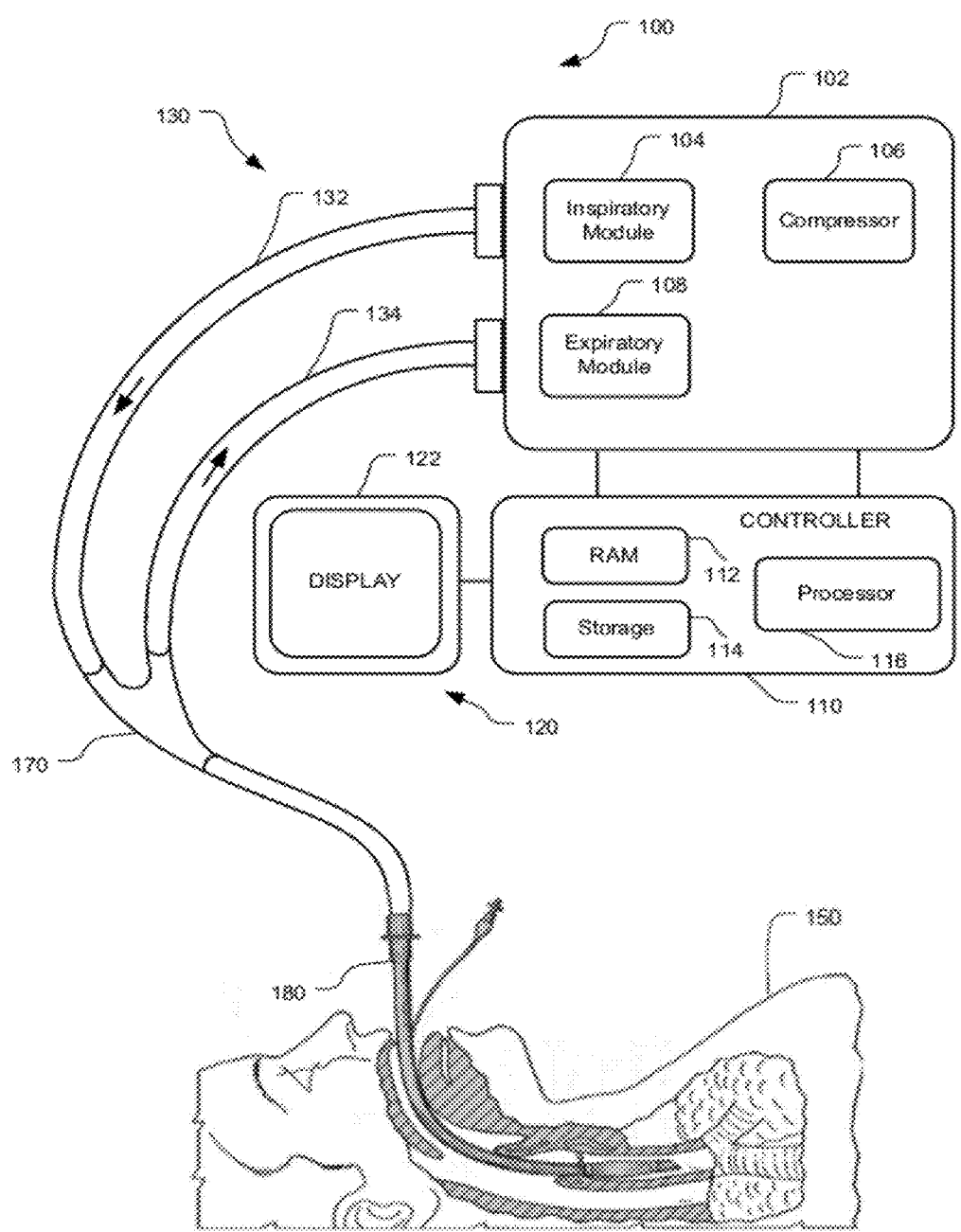
FIG. 1 is a diagram illustrating an embodiment of an exemplary ventilator connected to a human patient.

FIG. 1 is a diagram illustrating an embodiment of an exemplary ventilator connected to a human patient.

FIG. 1 illustrates ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive (e.g., endotracheal tube, as shown) or a non-invasive (e.g., nasal mask) patient interface.

Ventilation tubing system 130 may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory limb 132.

The pneumatic system 102 may include a variety of other components, including mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display to serve both as an input and output device.

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to one or more processors 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the one or more processors 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory system or between the ventilatory system and other therapeutic equipment and/or remote monitoring systems may be conducted over a distributed network, as described further herein, via wired or wireless means. Further, the present methods may be configured as a presentation layer built over the TCP/IP protocol. TCP/IP stands for "Transmission Control Protocol/Internet Protocol" and provides a basic communication language for many local networks (such as intra- or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Ventilator Components

Figure 2:
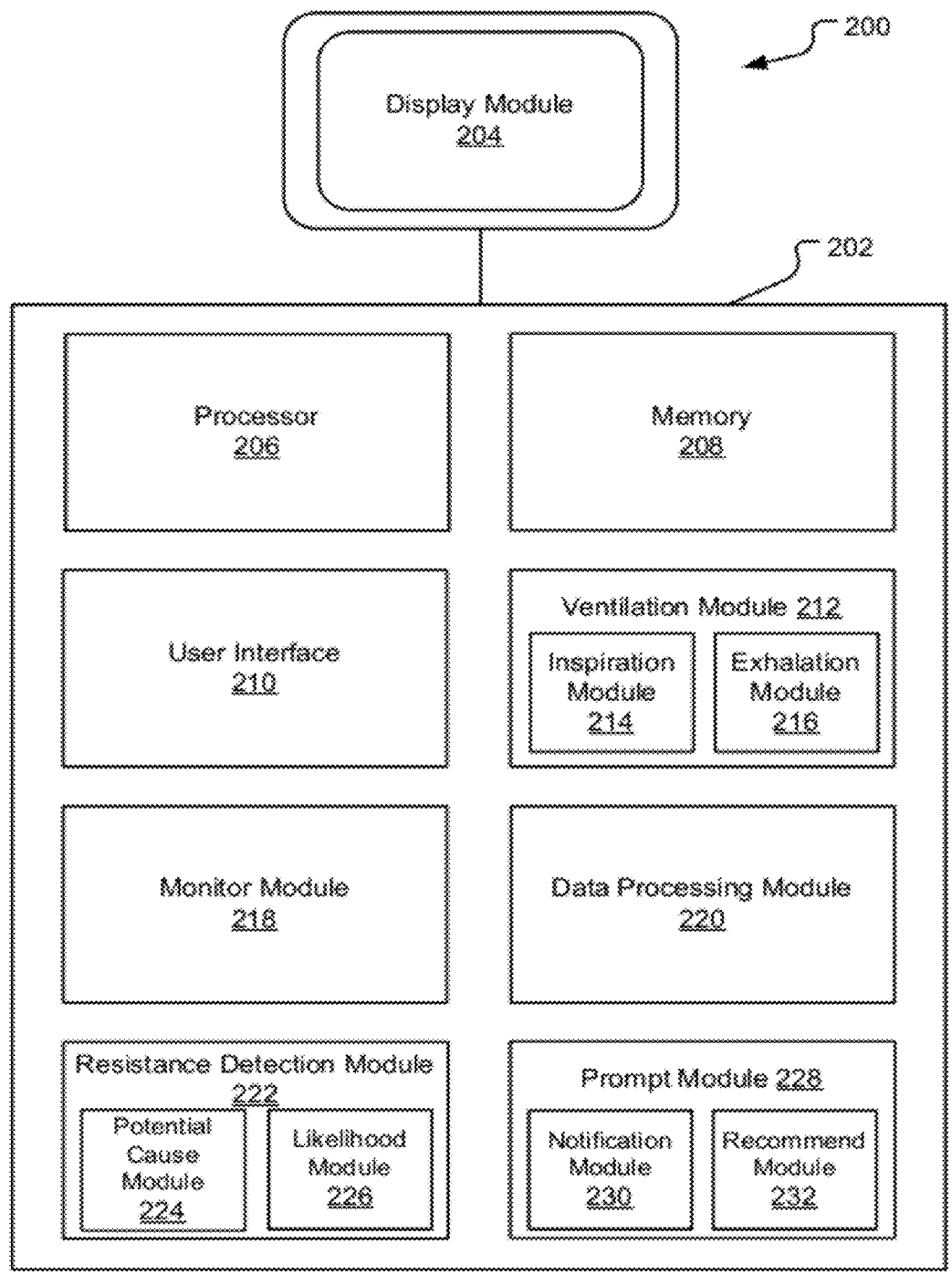
FIG. 2 is a block-diagram illustrating an embodiment of a ventilatory system for monitoring and evaluating ventilatory parameters associated with fluctuations in resistance.

FIG. 2 is a block-diagram illustrating an embodiment of a ventilatory system for monitoring and evaluating ventilatory parameters associated with fluctuations in resistance.

Ventilatory system 200 includes ventilator 202 with its various modules and components. That is, ventilator 202 may further include, inter alia, memory 208, one or more processors 206, user interface 210, and ventilation module 212 (which may further include an inspiration module 214 and an exhalation module 216). According to embodiments, the exhalation module 216 may be associated with an expiratory filter for preventing mucous and other debris from passing into the ventilator. Memory 208 is defined as described above for memory 112. Similarly, the one or more processors 206 are defined as described above for one or more processors 116. Processors 206 may further be configured with a clock whereby elapsed time may be monitored by the system 200.

The ventilatory system 200 may also include a display module 204 communicatively coupled to ventilator 202. Display module 204 may provide various input screens, for receiving clinician input, and various display screens, for presenting useful information to the clinician. The display module 204 is configured to communicate with user interface 210 and may include a graphical user interface (GUI). The GUI may be an interactive display, e.g., a touch-sensitive screen or otherwise, and may provide various windows and elements for receiving input and interface command operations. Alternatively, other suitable means of communication with the ventilator 202 may be provided, for instance by a wheel, keyboard, mouse, or other suitable interactive device. Thus, user interface 210 may accept commands and input through display module 204. Display module 204 may also provide useful information in the form of various data regarding the physical condition of a patient and/or a prescribed respiratory treatment. The useful information may be based on data collected by monitor module 218 or data derived or otherwise processed by data processing module 220, and the useful information may be displayed to the clinician in the form of graphs, wave representations, pie graphs, or other suitable forms of graphic display. For example, one or more smart prompts may be displayed on the GUI of display module 204 upon detection of a fluctuation in resistance by the ventilator. Additionally or alternatively, one or more smart prompts may be communicated to a remote monitoring system coupled via any suitable means to the ventilatory system 200.

Equation of Motion

Ventilation module 212 may oversee ventilation of a patient according to prescribed ventilatory settings. By way of general overview, the basic elements impacting ventilation may be described by the following ventilatory equation (also known as the Equation of Motion):

$$P_m + P_v = V_T/C + R \ast F$$

Here, $P_m$ is a measure of muscular effort that is equivalent to the pressure generated by the muscles of a patient. If the patient's muscles are inactive, the $P_m$ is equivalent to 0 cm $H_2O$. During inspiration, $P_v$ represents the positive pressure delivered by a ventilator (generally in cm $H_2O$). $V_T$ represents the tidal volume delivered based on the pressure supplied, C refers to the compliance, R represents the resistance, and F represents the gas flow during inspiration (generally in liters per min (L/m)). Alternatively, during exhalation, the Equation of Motion may be represented as:

$$P_a + P_t = V_{TE}/C + R \ast F$$

Here, $P_a$ represents the positive pressure existing in the lungs (generally in cm $H_2O$), $P_t$ represents the transairway pressure, $V_{TE}$ represents the tidal volume exhaled, C refers to the compliance, R represents the resistance, and F represents the gas flow during exhalation (generally in liters per min (L/m)).

Pressure

For positive pressure ventilation, pressure at the upper airway opening (e.g., in the patient's mouth) is positive relative to the pressure at the body's surface (i.e., relative to the ambient atmospheric pressure to which the patient's body surface is exposed, about 0 cm $H_2O$). As such, when $P_v$ is zero, i.e., no ventilatory pressure is being delivered, the upper airway opening pressure will be equal to the ambient pressure (i.e., about 0 cm $H_2O$). However, when inspiratory pressure is applied (i.e., positive pressure), a pressure gradient is created that allows gases to flow into the airway and ultimately into the lungs of a patient during inspiration (or, inhalation) until the pressure is equalized. When an inspiratory volume (or $V_T$) has been delivered to the lungs such that the inspiratory pressure is achieved and maintained, pressure is equalized and gases no longer flow into the lungs (i.e., zero flow).

Flow and Volume

Volume refers to the amount of gas delivered to a patient's lungs, usually in liters (L). Flow refers to a rate of change in volume over time ($F = \Delta V/\Delta t$). Flow is generally expressed in liters per minute (L/m or lpm) and, depending on whether gases are flowing into or out of the lungs, flow may be referred to as inspiratory flow or expiratory flow, respectively. According to embodiments, the ventilator may control the rate of delivery of gases to the patient, i.e., inspiratory flow, and may control the rate of release of gases from the patient, i.e., expiratory flow.

As may be appreciated, volume and flow are closely related. That is, where flow is known or regulated, volume may be derived based on elapsed time. Indeed, volume may be derived by integrating the flow waveform. According to embodiments, a tidal volume, $V_T$, may be delivered upon reaching a set inspiratory time ($T_I$) at set inspiratory flow. Alternatively, set $V_T$ and set inspiratory flow may determine the amount of time required for inspiration, i.e., $T_I$.

Compliance

Additional ventilatory parameters that may be measured and/or derived may include compliance and resistance, which refer to the load against which the patient and/or the ventilator must work to deliver gases to the lungs. Generally, compliance refers to a relative ease with which something distends and is the inverse of elastance, which refers to the tendency of something to return to its original form after being deformed. As related to ventilation, compliance refers to the lung volume achieved for a given amount of delivered pressure ($C = \Delta V/\Delta P$). Increased compliance may be detected when the ventilator measures an increased volume relative to the given amount of delivered pressure. Some lung diseases (e.g., acute respiratory distress syndrome (ARDS)) may decrease compliance and, thus, require increased pressure to inflate the lungs. Alternatively, other lung diseases may increase compliance, e.g., emphysema, and may require less pressure to inflate the lungs.

Resistance

Resistance refers to frictional forces that resist airflow, e.g., due to synthetic structures (e.g., endotracheal tube, expiratory valve, etc.), anatomical structures (e.g., bronchial tree, esophagus, etc.), or viscous tissues of the lungs and adjacent organs. Resistance is highly dependant on the diameter of the airway. That is, a larger airway diameter entails less resistance and a higher concomitant flow. Alternatively, a smaller airway diameter entails higher resistance and a lower concomitant flow. In fact, decreasing the diameter of the airway results in an exponential increase in resistance (e.g., two-times reduction of diameter increases resistance by sixteen times). As may be appreciated, resistance may also increase due to a restriction of the airway that is the result of, inter cilia, increased secretions, bronchial edema, mucous plugs, brochospasm, and/or kinking of the patient interface (e.g., invasive endotracheal or tracheostomy tubes).

Airway resistance may further be represented mathematically as:

$$R = P_t / F$$

Where $P_t$ refers to the transairway pressure and F refers to the flow. That is, $P_t$ refers to the pressure necessary to overcome resistive forces of the airway. Resistance may be expressed in centimeters of water per liter per second (i.e., cm $H_2O/L/s$).

Pulmonary Time Constant

As discussed above, compliance refers to the lung volume achieved for a given amount of delivered pressure ($C = \Delta V / \Delta P$). That is, stated differently, volume delivered is equivalent to the compliance multiplied by the delivered pressure ($\Delta V = C \cdot \Delta P$). However, as the lungs are not perfectly elastic, a period of time is needed to deliver the volume $\Delta V$ at pressure $\Delta P$. A pulmonary time constant, $\tau$, may represent a time necessary to inflate or exhale a given percentage of the volume at delivered pressure $\Delta P$. The pulmonary time constant, $\tau$, may be calculated by multiplying the resistance by the compliance ($\tau = R \cdot C$) for a given patient and z is generally represented in seconds, s. The pulmonary time constant associated with exhalation of the given percentage of volume may be termed an expiratory time constant and the pulmonary time constant associated with inhalation of the given percentage of volume may be termed an inspiratory time constant.

According to some embodiments, when expiratory resistance data is available, the pulmonary time constant may be calculated by multiplying expiratory resistance by compliance. According to alternative embodiments, the pulmonary time constant may be calculated based on inspiratory resistance and compliance. According to further embodiments, the expiratory time, $T_E$, should be equal to or greater than a predetermined number of pulmonary time constants (e.g., about three pulmonary time constants) to ensure adequate exhalation. The predetermined number of pulmonary time constants may be selected via any suitable means, e.g., a standard protocol, an institutional protocol, clinician input, etc. According to embodiments, for a triggering patient, $T_E$ (e.g., determined by trending $T_E$ or otherwise) should be equal to or greater than the predetermined number of pulmonary time constants. For a non-triggering patient, set RR should yield a $T_E$ that is equal to or greater than the predetermined number of pulmonary time constants.

Normal Resistance and Compliance

According to embodiments, normal resistance and compliance may be determined based on a patient's predicted body weight (PBW) (or ideal body weight (IBW)). That is, according to a standardized protocol or otherwise, patient data may be compiled such that normal resistance and compliance values and/or ranges of values may be determined and provided to the ventilatory system. As such, a manufacturer, clinical facility, clinician, or otherwise, may configure the ventilator with normal resistance and compliance values and/or ranges of values based on PBWs (or IBWs) of a patient population. Thereafter, during ventilation of a particular patient, resistance and compliance data may be trended for the patient and compared to normal values and/or ranges of values based on the particular patient's PBW (or IBW). According to embodiments, the ventilator may give an indication to the clinician regarding whether the trended resistance and compliance data of the particular patient falls into normal ranges. According to some embodiments, data may be more readily available for trending resistance and compliance for non-triggering patients than for triggering patients.

According to further embodiments, a predicted $T_E$ may be determined based on a patient's PBW (or IBW). That is, according to a standardized protocol or otherwise, patient population data may be compiled such that predicted $T_E$ values and/or ranges of values may be determined based on PBWs (or IBWs) of the patient population and provided to the ventilatory system. Actual (or trended) $T_E$ for a particular patient may then be compared to the predicted $T_E$. As noted previously, increased resistance and/or compliance may result in an actual $T_S$ that is longer than predicted $T_E$. However, when actual $T_E$ is consistent with predicted $T_E$, this may indicate that resistance and compliance for the particular patient fall into normal ranges.

According to further embodiments, a normal pulmonary time constant, $\tau$, may be determined based on a patient's PBW (or IBW). That is, according to a standardized protocol or otherwise, patient data may be compiled such that normal $\tau$ values and/or ranges of values may be determined based on PBWs (or IBWs) of a patient population and provided to the ventilatory system. A calculated $\tau$ may be determined for a particular patient by multiplying resistance by compliance (as described above, resistance and compliance data may be more readily available for a non-triggering patient). As the product of resistance and compliance results in $\tau$, increased resistance and/or compliance may result in an elevated $\tau$ value. However, when the calculated t value for the particular patient is consistent with the normal $\tau$ value, this may indicate that the resistance and compliance of the particular patient fall into normal ranges.

Patient Data

According to embodiments, patient data may be received by the ventilator 202. Patient data (including a patient diagnosis, a patient disability, a patient post-operative condition, a patient body weight, a patient gender, a patient age, etc.) may influence the ventilator's determination of the one or more causes for fluctuations in resistance. Furthermore, patient data may influence the ventilator's determination of one or more appropriate recommendations for mitigating the fluctuation in resistance. As such, according to some embodiments, the ventilator may take into consideration patient data when determining potential causes and/or recommendations for fluctuations in resistance.

Some patients may exhibit certain characteristics associated with various conditions and diseases, e.g., COPD, ARDS, post-operative condition (single lung, cardiac surgery), etc. For example, patients diagnosed with COPD may exhibit chronic elevated resistance due to constricted and/or collapsed airways, while ARDS patients may exhibit chronic elevated resistance due to an inflammatory condition of the airways. In some cases, patients diagnosed with various conditions and diseases associated with an obstructive component may exhibit elevated resistance over many months or years. According to some embodiments, patients having these conditions may also exhibit elevated compliance.

According to embodiments described herein, a clinician may input a patient diagnosis, e.g., COPD, ARDS, emphysema, etc. The ventilator may associate the patient diagnosis with certain lung and airway characteristics. For example, if the ventilator receives a patient diagnosis of COPD, the ventilator may associate this patient diagnosis with elevated resistance. The ventilator may further associate this patient diagnosis with an obstructive component. Alternatively, if the ventilator receives a patient diagnosis of emphysema, the ventilator may associate this patient diagnosis with elevated compliance. Alternatively still, a patient diagnosis of ARDS may be associated with increased resistance and/or decreased lung compliance.

Inspiration

Ventilation module 212 may further include an inspiration module 214 configured to deliver gases to the patient according to prescribed ventilatory settings. Specifically, inspiration module 214 may correspond to the inspiratory module 104 or may be otherwise coupled to source(s) of pressurized gases (e.g., air, oxygen, and/or helium), and may deliver gases to the patient. Inspiration module 214 may be configured to provide ventilation according to various ventilatory modes, e.g., via volume-targeted, pressure-targeted, or via any other suitable mode of ventilation.

According to embodiments, the inspiration module 214 may provide ventilation via a form of volume ventilation. Volume ventilation refers to various forms of volume-targeted ventilation that regulate volume delivery to the patient. Different modes of volume ventilation are available depending on the specific implementation of volume regulation. For example, for volume-cycled ventilation, an end of inspiration is determined based on monitoring the volume delivered to the patient. According to embodiments, during volume ventilation, as volume and flow are regulated by the ventilator, delivered $V_T$, flow waveforms (or flow traces), and volume waveforms may be constant and may not be affected by variations in lung or airway characteristics (e.g., compliance and/or resistance). Alternatively, pressure readings may fluctuate based on lung or airway characteristics. According to some embodiments, the ventilator may control the inspiratory flow and then derive volume based on the inspiratory flow and elapsed time. For volume-cycled ventilation, when the derived volume is equal to the prescribed $V_T$, the ventilator may initiate exhalation.

According to alternative embodiments, the inspiration module 214 may provide ventilation via a form of pressure ventilation. Pressure-targeted modes of ventilation may be provided by regulating the pressure delivered to the patient in various ways. For example, during pressure-cycled ventilation, an end of inspiration is determined based on monitoring the pressure delivered to the patient. According to embodiments, during pressure ventilation, the ventilator may maintain the same pressure waveform at the mouth, $P_{aw}$, regardless of variations in lung or airway characteristics, e.g., compliance and/or resistance. However, the volume and flow waveforms may fluctuate based on lung and airway characteristics. Under pressure-cycled ventilation, upon delivering the inspiratory pressure the ventilator may initiate exhalation.

As noted above, pressure delivered to the upper airway creates a pressure gradient that enables gases to flow into a patient's lungs. The pressure from which a ventilator initiates inspiration is termed the end-expiratory pressure (EEP) or "baseline" pressure. This pressure may be atmospheric pressure (about 0 cm $H_2O$), also referred to as zero end-expiratory pressure (ZEEP). However, commonly, the baseline pressure may be positive, termed positive end-expiratory pressure (PEEP). Among other things, PEEP may promote higher oxygenation saturation and/or may prevent airway collapse during exhalation. According to still other embodiments, a combination of volume and pressure ventilation may be delivered to a patient, e.g., volume-targeted-pressure-controlled (VC+) ventilation. In particular, VC+ventilation may provide benefits of setting a target $V_T$, while also allowing for monitoring variations in flow. As will be detailed further below, variations in flow may be indicative of various patient conditions.

Exhalation

Ventilation module 212 may further include an exhalation module 216 configured to release gases from the patient's lungs according to prescribed ventilatory settings. Specifically, exhalation module 216 may correspond to expiratory module 108 or may otherwise be associated with and/or controlling an expiratory valve for releasing gases from the patient. By way of general overview, a ventilator may initiate exhalation based on lapse of an inspiratory time setting ($T_I$) or other cycling criteria set by the clinician or derived from ventilator settings (e.g., detecting delivery of prescribed $V_T$ or prescribed inspiratory pressure based on a reference trajectory). Upon initiating the expiratory phase, exhalation module 216 may allow the patient to exhale by opening an expiratory valve. As such, exhalation is passive, and the direction of airflow, as described above, is governed by the pressure gradient between the patient's lungs (higher pressure) and the ambient surface pressure (lower pressure). Although expiratory flow is passive, it may be regulated by the ventilator based on the size of the expiratory valve opening. According to some embodiments, the expiratory valve may be associated with an expiratory filter. The expiratory filter may function to prevent mucous and other debris from passing into the ventilator. However, when the expiratory filter is obstructed, e.g., due to excess debris, mucous, etc., expiratory flow may be hindered. According to embodiments, the expiratory filter may be disposable or otherwise replaceable for eliminating excess debris, mucous, etc., that may increase resistance.

For a spontaneously breathing patient, expiratory time ($T_E$) is the time from the end of inspiration until the patient triggers a next inspiration. For a non-triggering patient, it is the time from the end of inspiration until the next mandatory inspiration based on the set RR. In some cases, however, the time required to return to the functional residual capacity (FRC) or resting capacity of the lungs is longer than provided by $T_E$ (e.g., because the pulmonary time constant has increased due to increased resistance, the expiratory filter is clogged hindering expiratory flow, etc.). According to embodiments, e.g., when the ventilator detects that resistance has increased as a result of changing lung conditions, various ventilatory settings may be adjusted to better match the time to reach FRC with the time available to reach FRC. For example, decreasing set $T_I$ to thereby increase the amount of time available to reach FRC. Alternatively, inspiratory pressure may be decreased (decreasing $V_T$), resulting in less time required to reach FRC. According to alternative embodiments, e.g., when the ventilator detects that the expiratory filter is clogged or that the patient airway may be obstructed by mucous, adjusting ventilatory settings may not be warranted. Rather, the ventilator may recommend to that the clinician change the expiratory filter or suction the patient airway.

As may be appreciated, at the point of transition between inspiration and exhalation, the direction of airflow may abruptly change from flowing into the lungs to flowing out of the lungs or vice versa depending on the transition. Stated another way, inspiratory flow may be measurable in the ventilatory circuit until $P_{Peak}$ is reached, at which point flow approximates zero. Thereafter, upon initiation of exhalation, expiratory flow is measurable in the ventilatory circuit until the pressure gradient between the lungs and the body's surface reaches zero (again, resulting in zero flow). However, in some cases, as will be described further herein, expiratory flow may still be positive, i.e., measurable, at the end of exhalation (termed positive end-expiratory flow or positive EEF). In this case, positive EEF is an indication that the pressure gradient has not reached zero or, similarly, that the patient has not completely exhaled. Thus, a positive EEF may indicate that the $T_E$ is not long enough for complete exhalation. According to some embodiments, when the ventilator detects that the $T_E$ is not long enough for complete exhalation, the ventilator may determine that the pulmonary time constant has increased due to increased resistance.

Ventilator Sensory Devices

The ventilatory system 200 may also include one or more distributed and/or internal sensors communicatively coupled to ventilator 202. Distributed sensors may communicate with various components of ventilator 202, e.g., ventilation module 212, internal sensors, monitor module 218, data processing module 220, and any other suitable components and/or modules. Distributed sensors may be placed in any suitable location, e.g., within the ventilatory circuitry or other devices communicatively coupled to the ventilator. For example, sensors may be affixed to the ventilatory tubing or may be imbedded in the tubing itself. According to some embodiments, sensors may be provided at or near the lungs (or diaphragm) for detecting a pressure in the lungs. Additionally or alternatively, sensors may be affixed or imbedded in or near wye-fitting 170 and/or patient interface 180, as described above.

Distributed sensors may further include pressure transducers that may detect changes in circuit pressure (e.g., electromechanical transducers including piezoelectric, variable capacitance, or strain gauge). Distributed sensors may further include various flow sensors for detecting airflow. For example, some flow sensors may use obstructions to create a pressure decrease corresponding to the flow across the device (e.g., differential pressure pneumotachometers) and other flow sensors may use turbines such that flow may be determined based on the rate of turbine rotation (e.g., turbine flow sensors). Alternatively, sensors may utilize optical or ultrasound techniques for measuring changes in ventilatory parameters. A patient's blood parameters or concentrations of expired gases may also be monitored by sensors to detect physiological changes that may be used as indicators to study physiological effects of ventilation, wherein the results of such studies may be used for diagnostic or therapeutic purposes. Indeed, any distributed sensory device useful for monitoring changes in measurable parameters during ventilatory treatment may be employed in accordance with embodiments described herein.

Ventilator 202 may further include one or more internal sensors. Similar to distributed sensors, internal sensors may communicate with various components of ventilator 202, e.g., ventilation module 212, distributed sensors, monitor module 218, data processing module 220, and any other suitable components and/or modules. Internal sensors may employ any suitable sensory or derivative technique for monitoring one or more parameters associated with the ventilation of a patient. However, the one or more internal sensors may be placed in any suitable internal location, such as, within the ventilatory circuitry or within components or modules of ventilator 202. For example, sensors may be coupled to the inspiratory and/or expiratory modules for detecting changes in, for example, circuit pressure and/or flow. Specifically, internal sensors may include pressure transducers and flow sensors for measuring changes in circuit pressure and airflow. Additionally or alternatively, internal sensors may utilize optical or ultrasound techniques for measuring changes in ventilatory parameters. For example, a patient's expired gases may be monitored by internal sensors to detect physiological changes indicative of the patient's condition and/or treatment, for example. Indeed, internal sensors may employ any suitable mechanism for monitoring parameters of interest in accordance with embodiments described herein.

As should be appreciated, with reference to the Equation of Motion, ventilatory parameters are highly interrelated and, according to embodiments, may be either directly or indirectly monitored. For example, the distributed and internal sensors may provide raw data to the monitor module 218. The raw data may further be provided to the data processing module 220 for processing and/or deriving ventilatory data. That is, parameters may be directly monitored by one or more sensors, as described above, or may be indirectly monitored by derivation according to the Equation of Motion or other equation, algorithm, etc.

Ventilatory Data

Ventilator 202 may further include a data processing module 220. As noted above, distributed sensors and internal sensors may collect data regarding various ventilatory parameters. A ventilatory parameter refers to any factor, characteristic, or measurement associated with the ventilation of a patient, whether monitored by the ventilator or by any other device. Sensors may further transmit collected data to the monitor module 218 and/or the data processing module 220. According to embodiments, the data processing module may 220 be configured to collect data regarding some ventilatory parameters, to derive data regarding other ventilatory parameters, and/or to transform the collected and/or derived ventilatory data into graphical data for display to the clinician and/or other modules of the ventilatory system. According to embodiments, the collected, derived, and/or graphically transformed data may be defined as ventilatory data. For example, data regarding end-expiratory flow (EEF), data regarding alveolar pressure $P_a$ (e.g., via a breath-hold maneuver), $P_{Peak}$ data, $P_{Plat}$ data, volume data, flow trace data, EEP data, etc., may be collected, derived, and/or graphically represented by data processing module 220. Thereafter, the ventilatory data may be utilized by the ventilator to detect a fluctuation, either an increase or a decrease, in resistance. Furthermore, the ventilatory data may be utilized by the ventilator to determine one or more potential causes for the fluctuation in resistance.

Furthermore, according to embodiments, ventilatory data may also include ventilator setup data. For example, ventilator setup data may include data regarding whether the ventilator is configured to use a heated or non-heated humidifier or a heat and moisture exchanger (HME). Furthermore, ventilator setup data may include data regarding whether an inline nebulizer or closed suction catheter is being used for the patient. Indeed, ventilator setup data may include any data regarding the configuration of the ventilator, ventilator circuitry, patient interface, etc., that may be useful for characterizing a detected fluctuation in resistance to determine one or more potential causes for the fluctuation in resistance. For example, ventilator setup data may be useful in determining whether condensate is likely to accumulate in the patient circuit, etc.

Upon detecting a fluctuation in resistance and one or more potential causes for the fluctuation, the ventilator may determine one or more recommendations for mitigating the fluctuation in resistance based on, inter cilia, ventilatory data, prescribed ventilatory settings, patient data, and/or any other suitable protocol, formula, equation, etc.

Flow Data

For example, according to embodiments, data processing module 220 may be configured to monitor inspiratory and expiratory flow. Flow may be measured by any appropriate, internal or distributed device or sensor within the ventilatory system. As described above, flow sensors may be employed by the ventilatory system to detect circuit flow. However, any suitable device either known or developed in the future may be used for detecting airflow in the ventilatory circuit. Data processing module 220 may be further configured to plot monitored flow data graphically via any suitable means. For example, according to embodiments, flow data may be plotted versus time (flow waveform), versus volume (flow-volume loop), or versus any other suitable parameter as may be useful to a clinician.

As may be appreciated, flow decreases as resistance increases, making it more difficult to pass gases into and out of the lungs (i.e., $F=P_t/R$). For example, when a patient is intubated, i.e., having either an endotracheal or a tracheostomy tube in place, resistance may be increased as a result of the smaller diameter of the tube over a patient's natural airway. In addition, increased resistance may be observed in patients with obstructive disorders, such as COPD, asthma, etc. Higher resistance may necessitate, inter alia, a higher inspiratory time setting ($T_I$) for delivering a prescribed pressure or volume of gases, a higher flow setting for delivering prescribed pressure or volume, a lower respiratory rate resulting in a higher expiratory time ($T_E$) for complete exhalation of gases, etc. According to embodiments, an evaluation of a flow trace and/or an evaluation of end-expiratory flow (EEF) may be used to detect an increase in resistance, as described further herein.

Pressure Data

According to embodiments, data processing module 220 may be configured to monitor pressure. Pressure may be measured by any appropriate, internal or distributed device or sensor within the ventilatory system. For example, pressure may be monitored by proximal electromechanical transducers connected near the airway opening (e.g., on the inspiratory limb, expiratory limb, at the patient interface, etc.). Alternatively, pressure may be monitored distally, at or near the lungs and/or diaphragm of the patient. As may be appreciated, an increase in transairway pressure may be indicative of an increase in resistance, while a decrease in transairway pressure may be indicative of an decrease in resistance (i.e., $R=P_t/F$)

Data processing module 220 may be further configured to graphically plot monitored pressure data via any suitable means. For example, according to embodiments, pressure data may be plotted versus time (pressure waveform), versus volume (pressure-volume loop or PV loop), or versus any other suitable parameter as may be useful to a clinician. According to embodiments, PV loops may provide useful clinical and diagnostic information to clinicians regarding the resistance or compliance of a patient. Specifically, upon comparing PV loops from successive breaths, an increase in resistance may be detected when successive PV loops shorten and widen over time. That is, at constant pressure, less volume is delivered to the lungs when resistance is increasing, resulting in a shorter, wider PV loop. According to alternative embodiments, a PV loop may provide a visual representation, in the area between the inspiratory plot of pressure vs. volume and the expiratory plot of pressure vs. volume, which is indicative of compliance. Further, PV loops may be compared to one another to determine whether compliance has changed. Additionally or alternatively, optimal compliance may be determined. That is, optimal compliance may correspond to the dynamic compliance determined from a PV loop during a recruitment maneuver, for example.

Volume Data

According to embodiments, data processing module 220 may be configured to derive volume via any suitable means. For example, as described above, during volume ventilation, a prescribed $V_T$ may be set for delivery to the patient. The actual volume delivered may be derived by monitoring the inspiratory flow over time (i.e., $V=F*T$). Stated differently, integration of flow over time will yield volume. According to embodiments, $V_T$ is completely delivered upon reaching $T_I$. Similarly, the expiratory flow may be monitored such that expired tidal volume ($V_{TE}$) may be derived. That is, under ordinary conditions, upon reaching the $T_E$, the prescribed $V_T$ delivered should be completely exhaled and FRC should be reached. However, under some conditions $T_E$ is inadequate for complete exhalation and FRC is not reached. Data processing module 220 may be further configured to graphically plot derived volume data via any suitable means. For example, according to embodiments, volume data may be plotted versus time (volume waveform), versus flow (flow-volume loop or FV loop), or versus any other suitable parameter as may be useful to a clinician.

Resistance Fluctuation Detection

Ventilator 202 may further include resistance detection module 222. According to embodiments, resistance detection module 222 may evaluate, inter cilia, the ventilatory data to detect a fluctuation in resistance. For example, based on PBW and/or other patient data, the resistance detection module 222 may identify a maximum resistance threshold and a minimum resistance threshold (e.g., based on clinician input, a standardized protocol, institutional protocol, etc.). According to embodiments, the maximum and minimum resistance thresholds may define a range about a particular patient's measured and/or derived resistance. That is, for a patient exhibiting elevated resistance (e.g., a patient diagnosed with ARDS or COPD), the maximum and minimum resistance thresholds may be higher than for a patient exhibiting normal resistance.

The resistance detection module 222 may further trend resistance values for the patient via any suitable means. "Trending," as used herein, means collecting and/or deriving data over a plurality of breaths (or at predetermined intervals of time). For example, according to embodiments, the resistance detection module 222 may trend resistance by evaluating a plurality of successive PV loops. According to alternative embodiments, the resistance detection module 222 may trend resistance by trending flow data at a constant pressure (e.g., during successive maneuvers). In this case, where other variables are known and/or constant, if flow decreases over time at constant pressure, resistance is increasing; whereas if flow is increasing over time at constant pressure, resistance is decreasing (i.e., $R=P_t/F$). According to alternative embodiments, a positive end expiratory flow may be indicative of increased resistance where expiratory time ($T_E$) is not sufficient to reach FRC. According to still other embodiments, resistance may be trended via any suitable means.

The trended resistance may be compared to the identified maximum and minimum threshold values to detect a fluctuation in resistance. When the trended resistance data breaches the maximum threshold value, the resistance detection module 222 may detect an increase in resistance. When the trended resistance data breaches the minimum threshold value, the resistance detection module 222 may detect a decrease in resistance.

Upon detection of a fluctuation in resistance, a potential cause determination module 224 may identify one or more potential causes for the fluctuation in resistance. For example, the potential cause determination module 224 may identify whether the fluctuation in resistance is an increase or a decrease. Furthermore, the potential cause determination module 224 may identify a location of the fluctuation in resistance. According to embodiments, the ventilator may be configured with one or more potential causes associated with an increase in resistance and with one or more potential causes associated with a decrease in resistance. Furthermore, the ventilator may be configured with one or more potential causes associated with a location of the fluctuation in resistance. For example, based on a protocol, standard, or otherwise, the ventilator may be configured to associate an increase in resistance with one or more of the following potential causes, among others: obstructed expiratory filter, obstructed ventilatory circuit (e.g., due to condensate accumulation, kinking, or otherwise), obstructed patient airway (e.g., due to mucus plugging), changing lung conditions (e.g., ARDS-related inflammatory response, asthma-related bronchial constriction, COPD-related airway constriction, bronchial edema, bronchospasm, infection and/or fluid, etc.), patient body position, poor internal placement of the ventilatory circuit, etc. For example, Indeed, the ventilator may be configured with any suitable number of potential causes associated with an increase in resistance. Furthermore, based on a protocol, standard, or otherwise, the ventilator may be configured to associate a decrease in resistance with one or more of the following potential causes: a leak in the ventilatory circuit, changing lung conditions (e.g., bronchial relaxation after medication, reduced infection and/or fluid, etc.), improved body position, etc. As above, the ventilator may be similarly configured with any suitable number of potential causes associated with a decrease in resistance.

According to embodiments, upon a determination that the fluctuation in resistance is an increase or a decrease and identification of one or more potential causes for the increase or decrease in resistance, a likelihood determination module 226 may be configured to determine a relative likelihood for each of the one or more identified potential causes. For example, likelihood determination module 226 may determine a relative likelihood for each of the one or more identified potential causes based on ventilatory data, patient data, sensory data, algorithms or other probability computations, etc. The likelihood determination module 226 may further rank or otherwise organize the one or more identified potential causes according to their relative likelihoods. For example, according to embodiments, the likelihood determination module 226 may be configured to determine a relative likelihood of one or more identified potential causes based on a location of the fluctuation in resistance. For example, when increased resistance was detected in the expiratory limb, it may be more likely that condensate accumulation in the ventilatory circuit or a clogged expiratory filter may be potential causes. Furthermore, according to embodiments, the likelihood determination module 226 may be configured to determine a relative likelihood that the expiratory filter is obstructed based on one or more of the following (among others): data from a sensory device at or near the expiratory valve, an evaluation of when the expiratory filter was last replaced, an evaluation of expiratory flow, etc. That is, according to embodiments, the ventilator may detect increased resistance in the expiratory limb of the ventilatory circuit indicative of a clogged expiratory filter.

According to embodiments, the ventilator may be further configured to determine a relative likelihood that the patient circuit is occluded. For example, an abrupt increase in resistance may be indicative of a ventilatory circuit that is kinked or otherwise temporarily occluded. In contrast, a gradual increase in resistance may be indicative of mucous plugging (among other causes). For example, the ventilator may detect mucous plugging in the patient's airway via one or more distributed sensory devices, a length of time since the patient airway was last suctioned, increased resistance to delivered flow to the patient, etc. According to other embodiments, the ventilator may be configured to determine a relative likelihood that decreased resistance is due to a leak in the ventilatory circuit. For instance, ventilator may evaluate one or more of the following (among others): whether delivered volume is less than the expired volume, data collected by distributed sensors along the ventilatory circuit, trended flow data, etc.

According to some embodiments, the likelihood determination module 226 may further evaluate patient data and/or a patient diagnosis to determine whether certain changed lung conditions are likely responsible for a fluctuation in resistance. For example, if patient data indicates that the patient is asthmatic, the ventilator may determine a higher relative likelihood that bronchial constriction is a potential cause for an increase in resistance. In contrast, if the patient has been diagnosed with ARDS, the ventilator may determine a higher relative likelihood that an increase in inflammation of the airways is a potential cause for the increase in resistance. Alternatively, if the patient was diagnosed with pneumonia, the ventilator may determine a higher relative likelihood that a reduction in infection and/or fluid in the patient's lungs is a potential cause for a decrease in resistance (or that an increase in infection and/or fluid in the lungs is a potential cause for an increase in resistance). Indeed, each identified potential cause may be associated with a relative likelihood based on any available ventilatory data, sensory data, patient data, etc., retrieved by the ventilator. According to embodiments, the ventilator may determine that more than one potential cause may have a same or similar relative likelihood for causing an increase or a decrease in resistance.

According to some embodiments, the ventilator may display each of the one or more identified potential causes to the clinician. According to other embodiments, the ventilator may only display a subset of the one or more identified potential causes, e.g., only potential causes having higher relative likelihoods. The ventilator may be configured to determine and display the subset of identified potential causes via any suitable means. For example, the ventilator may be configured to display a predetermined number of the most likely potential causes, e.g., the three most likely potential causes. In this case, the ventilator will display the three most likely potential causes of three identified potential causes, of five identified potential causes, or of ten identified potential causes. As may be appreciated, any number of the most likely potential causes may be pre-configured, selected, or otherwise designated for display. According to alternative embodiments, the ventilator may be configured to display a most likely percentage of identified potential causes. For example, the ventilator may be configured to display the most likely 40% of potential causes. In this case, the most likely 4 of 10 identified potential causes, the most likely 2 of 5 identified potential causes, etc. (here, the ventilator may be further configured to round up or down to the nearest whole number of potential causes for display). According to still other embodiments, each potential cause may be designated with a likelihood probability upon evaluation of ventilatory data, patient data, statistical analyses, etc. (e.g., a likelihood probability between 1 and 100) and the ventilator may be configured to display only those potential causes with a likelihood probability greater than some number (e.g., a likelihood probability of 50 or more). Indeed, any suitable method for ranking, organizing, or otherwise identifying and displaying one or more likely potential causes for an increase or a decrease in resistance may be employed within the spirit of the present disclosure.

Prompt Generation

Ventilator 202 may further include a prompt module 228. The prompt module 228 may provide a prompt notifying a clinician of a detected increase or decrease in resistance. According to some embodiments, the prompt may be provided in a hierarchical format such that an initial prompt is displayed that provides a notification to the clinician that an increase or a decrease in resistance has been detected. The initial prompt may further provide an indication of the one or more identified potential causes for the increase or decrease in resistance. Alternatively, the initial prompt may only display a subset of the identified potential causes, i.e., the most likely potential causes. According to other embodiments, the initial prompt may only display a notification that an increase or a decrease in resistance has been detected and the one or more potential causes may be displayed on an expanded prompt.

According to embodiments, the prompt module 228 may provide the initial prompt as a tab, banner, dialog box, or other suitable type of display. The initial prompt may be provided along a border of the graphical user interface, near an alarm display or bar, or in any other suitable location. A shape and size of the initial prompt may further be optimized for easy viewing with minimal interference to other ventilatory displays. The initial prompt may be further configured with a combination of icons and text such that the clinician may readily identify whether resistance has increased or decreased and, optionally, one or more potential causes for the increase or decrease in resistance. According to some embodiments, the initial prompt may display only one or more potential causes having a higher relative likelihood for causing the increase or decrease in resistance.

According to further embodiments, the prompt module 228 may provide an expanded prompt via any suitable means. For example, the expanded prompt may be selectably activated via any suitable means and may display the one or more identified potential causes and/or one or more recommendations for mitigating the increase or decrease in resistance. The expanded prompt may further be provided adjacent to the prompt (i.e., initial prompt) along a border of the graphical user interface, near an alarm display or bar, or in any other suitable location. The shape and size of the expanded prompt may further be optimized for easy viewing with minimal interference to other ventilatory displays.

Prompt module 228 may also provide the initial prompt and/or expanded prompt as a partially transparent window or format. The transparency may allow for the initial prompt and/or expanded prompt to be displayed such that normal ventilator GUI and ventilatory data may be visualized behind the prompts. This feature may be particularly useful for displaying the expanded prompt. The initial prompt and/or expanded prompt may further be displayed in areas of the user interface that are either blank or that cause minimal distraction from the ventilatory data and other graphical representations provided by the GUI. However, upon selective expansion of an initial prompt, data and graphs may be at least partially obscured. As a result, prompt module 228 may provide the expanded prompt such that it is partially transparent.

The prompt module 228 may further include a notification module 230. The notification module 230 may identify a fluctuation in resistance via any suitable means. For example, the notification module 230 may be in communication with the resistance detection module 222, the monitor module 218, the data processing module 220, and/or any other suitable module or sensory device to identify that a fluctuation in resistance has been detected by the ventilator. Further, the notification module 230 may identify whether the fluctuation in resistance is an increase or a decrease and a location in the ventilatory system where the fluctuation in resistance was detected. According to embodiments, the notification module 230 may further identify one or more potential causes for the increase or decrease in resistance. For example, the notification module 230 may be in communication with the potential cause determination module 224 or any other suitable module or sensory device. According to further embodiments, the notification module 230 may identify a relative likelihood of each of the one or more identified potential causes. For example, the notification module 230 may be in communication with the likelihood determination module 226 or any other suitable module or sensory device. According to embodiments, the notification module 230 may further provide an indication of the increase or decrease in resistance to the prompt module 228 for display on a prompt. According to additional embodiments, the notification module 230 may further provide an indication of the one or more potential causes for the increase or the decrease in resistance, or a subset thereof, to the prompt module 228 for display on a prompt.

The prompt module 228 may further include a recommendation module 232. That is, according to embodiments, in addition to identifying one or more potential causes for an increase or a decrease in resistance, the ventilator may also determine one or more recommendations for mitigating the increase or decrease in resistance. For example, prompt module 228 may be configured to display the one or more recommendations on a prompt on user interface 204, e.g., within a window of the GUI. According to additional embodiments, the prompt may be communicated to and/or displayed on a remote monitoring system communicatively coupled to ventilatory system 200.

According to embodiments, the recommendation module 232 may retrieve one or more potential causes for the increase or decrease in resistance from the potential cause determination module 224 or, according to some embodiments, the recommendation module 232 may retrieve only one or more potential causes having a higher relative likelihood of causing the increase or decrease in resistance from the likelihood determination module 226. As may be appreciated, the ventilator may be configured to associate some potential causes for an increase or a decrease in resistance with one or more appropriate recommendations for mitigating the increase or decrease in resistance. In contrast, for other potential causes, it may not be appropriate or necessary to mitigate the increase or decrease in resistance (e.g., where a decrease in resistance is detected upon administration of medication for bronchial constriction).

According to embodiments, the recommendation module 232 may be configured to determine one or more appropriate recommendations for mitigating an increase or a decrease in resistance based on an evaluation of ventilatory data, patient data, sensory data, current ventilatory settings, and any suitable protocol, equation, etc. For example, the ventilator may evaluate each potential cause (or each of the more likely potential causes) in light of data known to the ventilator in order to determine one or more recommendations for mitigating the increase or decrease in resistance. That is, if the ventilator determines that it is relatively likely that a dirty expiratory filter caused an increase in resistance, the ventilator may determine that it is appropriate to recommend changing the expiratory filter. In contrast, if the ventilator determines that it is relatively likely that a kink or temporary occlusion of the ventilatory circuit caused an increase in resistance, the ventilator may determine that it is appropriate to recommend checking the ventilatory circuit for kinking. Alternatively, if the ventilator determines that it is relatively likely that bronchial constriction is a cause for an increase in resistance (e.g., for an asthmatic patient), the ventilator may determine that it is appropriate to recommend administration of medication to the patient (here, the ventilator may be further configured to evaluate the last time that medication was administered prior to determining the appropriate recommendation). In contrast, if the patient has been diagnosed with COPD, the ventilator may determine that it is appropriate to recommend increasing PEEP in order to promote bronchial patency.

As specified above, in some cases a recommendation may not be warranted. For example, if the ventilator determines that administration of medication is a likely cause of a decrease in resistance, the ventilator may not provide a recommendation but may merely notify the clinician of the decreased resistance. Similarly, if the ventilator senses a decrease in resistance following suctioning of the patient airway, the ventilator may merely notify the clinician of the decrease rather than offering a recommendation for mitigating the decrease in resistance. As may be appreciated, the one or more recommendations may be based on a variety of considerations, including whether the resistance increased or decreased, on potential causes for the increase or decrease in resistance, and on available ventilatory data, patient data, sensory data, and any suitable protocol, equation, etc. Indeed, as should be appreciated, any number of appropriate recommendations may be determined based on each of a plurality of potential causes for the increase or decrease in resistance.

In order to accomplish the various aspects of the notification and/or recommendations display, the prompt module 228 may communicate with various other components and/or modules. For instance, prompt module 228 may be in communication with monitor module 218, data processing module 220, resistance detection module 224, potential cause determination module 224, likelihood determination module 226, notification module 230, recommendation module 232, and/or any other suitable module or component of the ventilatory system 200. That is, prompt module 228 may receive ventilatory data, sensory data, and information regarding any suitable protocol, equation, etc. Further, according to some embodiments, the prompt module 228 may have access to patient data, including a patient's diagnostic information (e.g., regarding whether the patient has ARDS, COPD, asthma, emphysema, or any other disease, disorder, or condition).

According to embodiments, upon viewing an initial prompt and/or expanded prompt in response to detection of an increase or decrease in resistance, the initial prompt and/or expanded prompt may be cleared from the graphical user interface.

Methods of Prompt Generation

Figure 3:
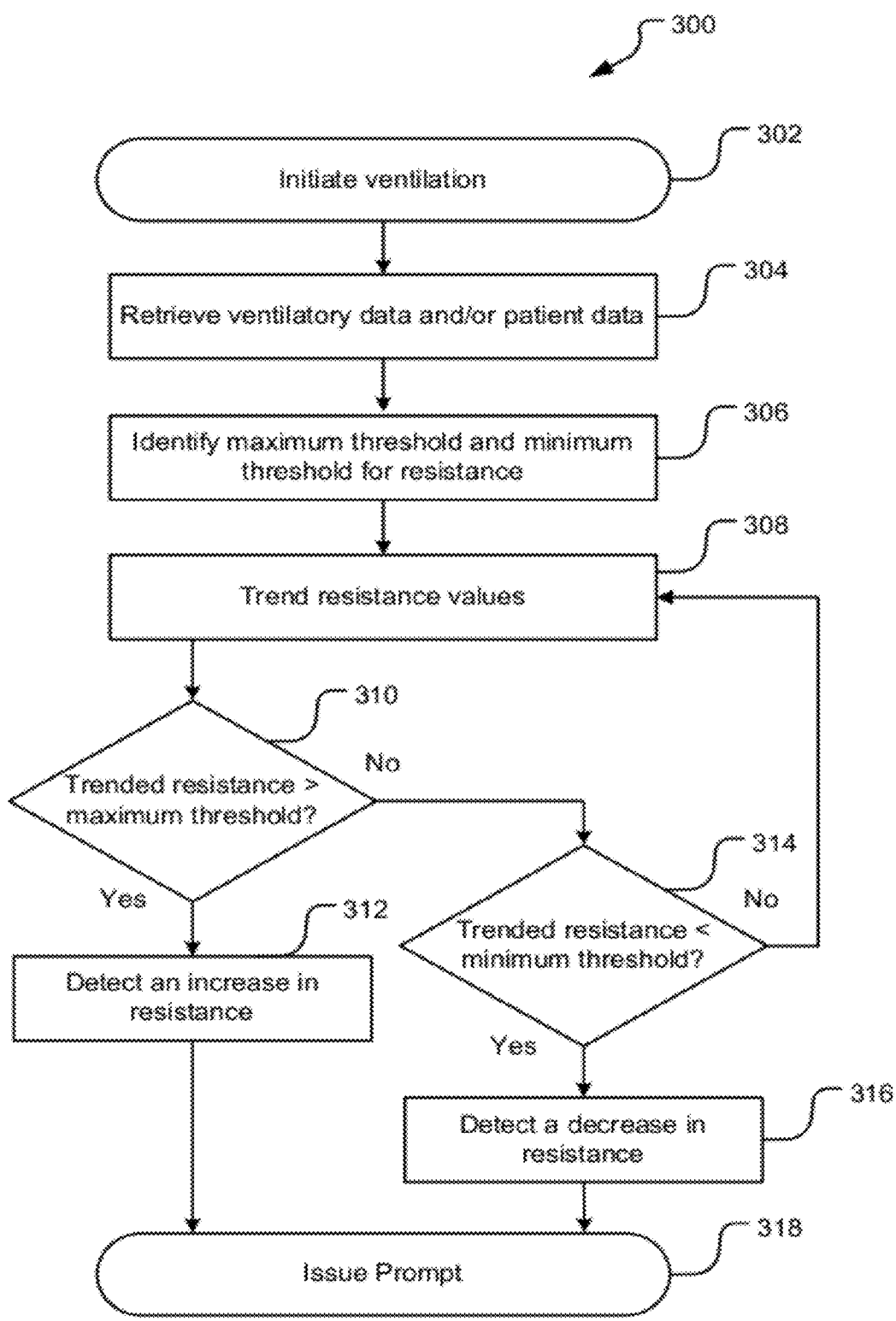
FIG. 3 is a flow chart illustrating an embodiment of a method for issuing a prompt upon detecting an increase or a decrease in resistance.

FIG. 3 is a flow chart illustrating an embodiment of a method for issuing a prompt upon detecting an increase or a decrease in resistance.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

Method 300 begins with an initiate ventilation operation 302. Initiate ventilation operation 302 may further include various additional operations. For example, initiate ventilation operation 302 may include receiving one or more ventilatory settings associated with ventilation of a patient. As such, the ventilatory settings and/or input received may include, inter alia, an inspiratory pressure (or target inspiratory pressure), a tidal volume ($V_T$), a respiratory rate (RR), an I:E ratio, a % $O_2$, etc. Additionally, during ventilation, ventilatory settings may be adjusted and accepted. In addition, during initiate ventilation operation 302, patient data may be received. Patient data may refer to any data particular to a patient, for example, a predicted or ideal body weight (PBW or IBW), a patient diagnosis, a patient age, a patient disability, a patient post-operative condition, etc. A patient diagnosis may include, inter alia, ARDS, COPD, emphysema, asthma, etc. Upon initiating ventilation, the ventilator may further monitor ventilatory parameters and collect and/or derive ventilatory data.

At retrieve operation 304, the ventilator may retrieve ventilatory data, patient data, etc. The ventilatory data may include data collected while monitoring various ventilatory parameters, including volume, pressure, flow, etc. The ventilatory data may further include data that is calculated or otherwise derived from the collected data, e.g., via the Equation of Motion or otherwise. For example, resistance may be calculated or otherwise derived from collected data such as flow, pressure, or volume (e.g., $R=P_t/F$; $R=\tau^*\Delta P/\Delta V$; etc.) Furthermore, resistance may be derived at over a plurality of breaths or at predetermined intervals of time. The patient data may include, inter cilia, any data particular to a patient as described above.

At identify operation 306, the ventilator may identify a maximum resistance threshold and a minimum resistance threshold. For example, the maximum resistance threshold and a minimum resistance threshold may be based on PBW and/or other patient data (e.g., based on clinician input, a standardized protocol, institutional protocol, etc.). According to alternative embodiments, the maximum and minimum resistance thresholds may be defined for a particular patient. That is, based on an initial calculation of a particular patient's resistance, the maximum threshold may be set at a certain amount or percentage above the initial calculation and the minimum threshold may be set at a certain amount or percentage below the initial calculation. In this case, for a patient exhibiting elevated resistance (e.g., a patient diagnosed with ARDS or COPD), the maximum and minimum resistance thresholds may be higher than for a patient exhibiting normal resistance. According to alternative embodiments, the maximum and minimum resistance thresholds may be based at least in part on a patient diagnosis (e.g., based on clinician input, a standardized protocol, institutional protocol, etc.). In this case, as with the example above, the maximum and minimum resistance thresholds may be higher for a patient diagnosed with COPD than for a patient exhibiting normal resistance.

At trend operation 308, the ventilator may trend resistance. As described above, according to embodiments, the ventilator may trend resistance by evaluating a plurality of successive PV loops. As described above, an increase in resistance may be detected when successive PV loops shorten and widen over time. That is, at constant pressure, less volume is delivered to the lungs when resistance is increasing, resulting in a shorter, wider PV loop. According to alternative embodiments, the ventilator may trend resistance by trending flow data at a constant pressure (e.g., during successive maneuvers). In this case, where other variables are known and/or constant, if flow decreases over time at constant pressure, resistance is increasing; whereas if flow is increasing over time at constant pressure, resistance is decreasing (i.e., $R=P_i/F$). According to alternative embodiments, a positive end expiratory flow may be indicative of increased resistance where expiratory time ($T_E$) is not sufficient to reach FRC. According to other embodiments, calculated values for resistance may be trended over a period of time or over a number of breaths. According to still other embodiments, resistance may be trended via any suitable means. According to alternative embodiments, the ventilator may trend resistance values associated with a location. For example, the ventilator may monitor and trend resistance at or near the expiratory valve, within the expiratory limb or the inspiratory limb of the ventilatory circuit, within the patient airway, etc. According to some embodiments, different maximum and minimum resistance thresholds may apply based on the monitored location.

At determination operation 310, the ventilator may compare the trended resistance with the maximum threshold. If the trended resistance breaches the maximum threshold, the ventilator may detect an increase in resistance at detect operation 312. According to embodiments, the ventilator may further associate the increase in resistance with a location, e.g., patient airway, expiratory limb, etc.

At determination operation 314, the ventilator may compare the trended resistance with the minimum threshold. If the trended resistance breaches the minimum threshold, the ventilator may detect a decrease in resistance at detect operation 316. According to embodiments, the ventilator may further associate the decrease in resistance with a location, e.g., patient airway, expiratory limb, etc.

At issue prompt operation 318, the ventilator may issue a prompt providing a notification that an increase or a decrease in resistance was detected by any suitable means. For example, the ventilator may generate an alert or other notification in text form. For example, the notification may provide: "Increased Resistance Detected" or "Decreased Resistance Detected." According to alternative embodiments, the prompt may provide a notification via an abbreviated alert, an icon, or any other suitable method of notifying the clinician that an increase or a decrease in resistance was detected by the ventilator. As described above, the prompt may be displayed by any suitable means in any suitable location on the ventilator or a remote monitor. For example, the prompt may be displayed as a tab, banner, dialog box, or other suitable type of display, along a border of the graphical user interface, near an alarm display or bar, or in any other suitable location. The prompt may further be displayed in areas of the user interface that are either blank or that cause minimal distraction from the ventilatory data and other graphical representations provided by the GUI. The prompt may be provided in a transparent form, or otherwise, for minimizing distraction, and may be cleared upon clinician viewing.

Figure 4:
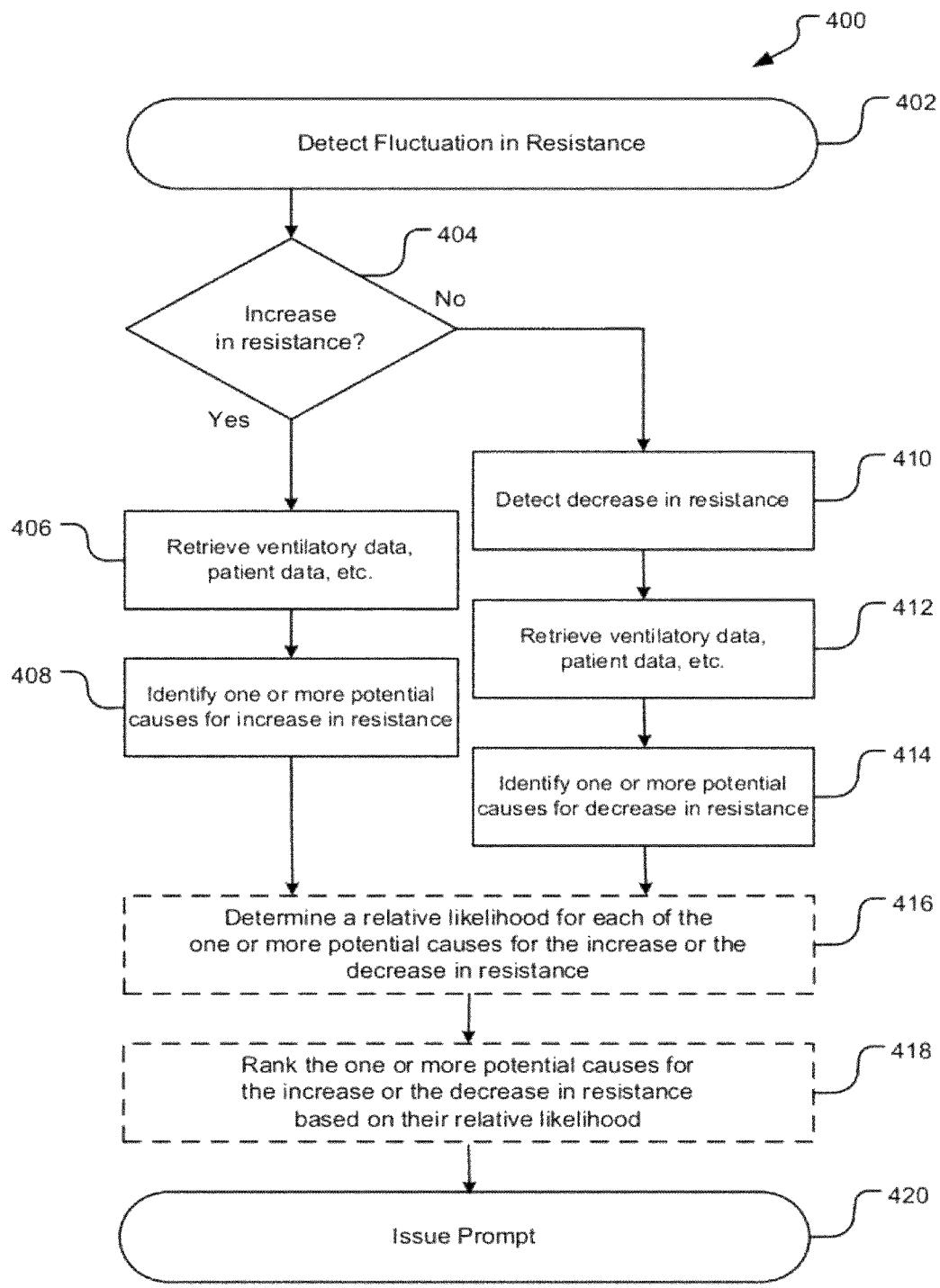
FIG. 4 is a flow chart illustrating an embodiment of a method for issuing a prompt upon determining one or more potential causes for an increase or a decrease in resistance.

FIG. 4 is a flow chart illustrating an embodiment of a method for issuing a prompt upon determining one or more potential causes for an increase or a decrease in resistance.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

Method 400 begins with detect fluctuation operation 402, wherein the ventilator detects a fluctuation in resistance, either an increase or a decrease, as described above with reference to method 300.

At determination operation 404, the ventilator may determine whether the fluctuation in resistance is an increase, as described above with reference to method 300.

Upon a determination that there was an increase in resistance, the method may proceed to retrieve operation 406. At retrieve operation 406, the ventilator may retrieve ventilatory data, patient data, and/or any other data, equation, protocol, standard, etc., as described with reference to operation 304. Furthermore, at identify operation 408, the ventilator may identify one or more potential causes for the increase in resistance. As described above, the ventilator may be configured with one or more potential causes associated with an increase in resistance. For example, based on a protocol, standard, or otherwise, the ventilator may be configured to associate an increase in resistance with one or more of the following potential causes, among others: obstructed expiratory filter, obstructed ventilatory circuit (e.g., due to condensate accumulation, kinking, or otherwise), obstructed patient airway (e.g., due to mucous plugging), changing lung conditions (e.g., asthma-related bronchial constriction, COPD-related airway constriction, ARDS-related inflammatory response, bronchial edema, bronchospasm, infection and/or fluid, etc.), poor patient body position, improper internal placement of the ventilatory circuit, etc. Indeed, the ventilator may be configured with any suitable number of potential causes associated with an increase in resistance.

Upon a determination that there was not an increase in resistance, the method may proceed to detect operation 410. At detect operation 410, the ventilator may determine that a decrease in resistance was detected.

Upon a determination that there was a decrease in resistance, the method may proceed to retrieve operation 412. At retrieve operation 412, the ventilator may retrieve ventilatory data, patient data, and/or any other data, equation, protocol, standard, etc., as described with reference to operation 304. Furthermore, at identify operation 414, the ventilator may identify one or more potential causes for the decrease in resistance. As described above, the ventilator may be configured with one or more potential causes associated with a decrease in resistance. For example, based on a protocol, standard, or otherwise, the ventilator may be configured to associate a decrease in resistance with one or more of the following potential causes: a leak in the ventilatory circuit, changing lung conditions (e.g., bronchial relaxation after medication, reduced infection and/or fluid, etc.), improved body position, etc. As above, the ventilator may be similarly configured with any suitable number of potential causes associated with a decrease in resistance.

At optional determine operation 416 (identified by dashed lines), the ventilator may optionally determine a relative likelihood for each of the one or more identified potential causes for the increase or the decrease in resistance, e.g., based on ventilatory data, patient data, sensory data, algorithms, statistical analyses, etc. For example, according to embodiments, the ventilator may be configured to determine a relative likelihood that the expiratory filter is obstructed based on one or more of the following (among others): data from a sensory device at or near the expiratory valve, an evaluation of when the expiratory filter was last replaced, an evaluation of expiratory flow, etc. According to some embodiments, the ventilator may detect an increase in expiratory limb resistance indicative of a clogged expiratory filter. The ventilator may be further configured to determine a relative likelihood that the ventilatory circuit is occluded. For example, an abrupt increase in resistance may be indicative of a ventilatory circuit that is kinked or otherwise temporarily occluded, and if so, the ventilator may be further configured to identify whether the inspiratory or expiratory limb is occluded. In contrast, a gradual increase in resistance may be indicative of mucous plugging in the patient airway or condensate accumulation in the ventilatory circuit. For example, the ventilator may detect mucous plugging in the patient airway via one or more distributed sensory devices, a length of time since the patient airway was last suctioned, increased resistance in the patient airway, etc. Alternatively, the ventilator may detect condensate accumulation in the ventilatory circuit via one or more distributed sensory devices, a length of time since the ventilatory circuit was drained of condensate, a type of humidifier utilized (e.g., heated or not), etc. As may be appreciated, the ventilator may be configured to determine a relative likelihood for each of the one or more potential causes for the increase or the decrease in resistance via any suitable means.

According to some embodiments, the ventilator may also evaluate patient data, including a patient diagnosis, to determine relative likelihoods for the one or more identified potential causes. For example, if the patient data indicates that the patient is asthmatic, the ventilator may determine a higher relative likelihood that bronchial constriction is a potential cause for an increase in resistance. In contrast, if the patient has been diagnosed with ARDS, the ventilator may determine a higher relative likelihood that an increase in inflammatory response is a potential cause for the increase in resistance. Alternatively, if the patient was diagnosed with pneumonia, the ventilator may determine a higher relative likelihood that a reduction in infection and/or fluid in the patient's lungs is a potential cause for a decrease in resistance (or that an increase in infection and/or fluid in the lungs is a potential cause for an increase in resistance). Indeed, each identified potential cause may be associated with a relative likelihood based on the specific ventilatory data, sensory data, patient data, etc., retrieved by the ventilator. According to embodiments, the ventilator may determine that more than one potential cause may have a same or similar relative likelihood for causing an increase or a decrease in resistance.

At optional determine operation 418 (identified by dashed lines), the ventilator may optionally rank or otherwise organize the one or more identified potential causes according to their relative likelihoods. For example, based on algorithms, statistical analyses, probability theorem, or otherwise, the ventilator may determine a probability that each of the one or more identified potential causes led to the increase or the decrease in resistance. For instance, according to embodiments, each potential cause may be designated with a likelihood probability upon evaluation of ventilatory data, patient data, computations, etc. (e.g., a likelihood probability between 1 and 100). According to alternative embodiments, the ventilator may simply rank each of the one or more identified potential causes according to their relative likelihoods, e.g., for 5 identified potential causes, the ventilator may rank each potential cause from 1, most likely, to 5, least likely. For potential causes that are determined to have a statistically equivalent likelihood, the ventilator may assign the same ranking. Indeed, the ventilator may be configured to rank or organize each of the identified potential causes for the increase or the decrease in resistance via any suitable means.

At issue prompt operation 420, the ventilator may issue a prompt displaying one or more potential causes for the increase or decrease in resistance via any suitable means. For example, the prompt may provide: "Increased Resistance Likely Due to Clogged Expiratory Filter," "Increased Resistance Likely Due to Bronchial Constriction," or "Decreased Resistance Likely Due to Response to Bronchodilator Therapy," etc. According to embodiments, the prompt may display one or more of the identified potential causes but less than all of the identified potential causes for the increase or the decrease in resistance. For example, according to some embodiments, the ventilator may display only a most likely potential cause on the prompt. For example, where the ventilator determines that an increase in resistance may be due to condensate accumulation in the ventilatory circuit or to a clogged expiratory filter, but where condensate accumulation is more likely, the prompt may display only: "Increase Resistance Detected, Condensate Accumulation Likely." According to alternative embodiments, the ventilator may be configured to display a predetermined number of the most likely potential causes, e.g., the three most likely potential causes. According to still alternative embodiments, the ventilator may be configured to display a most likely percentage of identified potential causes, e.g., the most likely 40% of potential causes. According to still alternative embodiments, the ventilator may be configured to display only those potential causes with a likelihood probability greater than some number (e.g., a likelihood probability of 50 or more). Indeed, the ventilator may be configured to display the one or more potential causes for the increase or decrease in resistance, or a subset thereof, according to any suitable method. According to at least some embodiments, the ventilator may determine one or more potential causes for the increase or decrease in resistance but may not display the one or more potential causes to the clinician.

As described above, the prompt may be displayed by any suitable means in any suitable location on the ventilator or a remote monitor. For example, the prompt may be displayed as a tab, banner, dialog box, or other suitable type of display, along a border of the graphical user interface, near an alarm display or bar, or in any other suitable location. The prompt may further be displayed in areas of the user interface that are either blank or that cause minimal distraction from the ventilatory data and other graphical representations provided by the GUI. The prompt may be provided in a transparent form, or otherwise, for minimizing distraction, and may be cleared upon clinician viewing.

According to some embodiments, the ventilator may display the one or more potential causes for the increase or decrease in resistance, or a subset thereof, on an expanded prompt. For example, the ventilator may notify the clinician of an increase or a decrease in resistance on an initial prompt. The initial prompt may provide an icon or other selectable control such that upon clinician selection the one or more potential causes for the increase or decrease in resistance may be displayed on an expanded prompt. The expanded prompt may further be provided adjacent to the initial prompt along a border of the graphical user interface, near an alarm display or bar, or in any other suitable location. The shape and size of the expanded prompt may further be optimized for easy viewing with minimal interference to other ventilatory displays. The initial prompt and/or expanded prompt may be provided in a transparent form, or otherwise, for minimizing distraction, and may be cleared upon clinician viewing.

Figure 5:
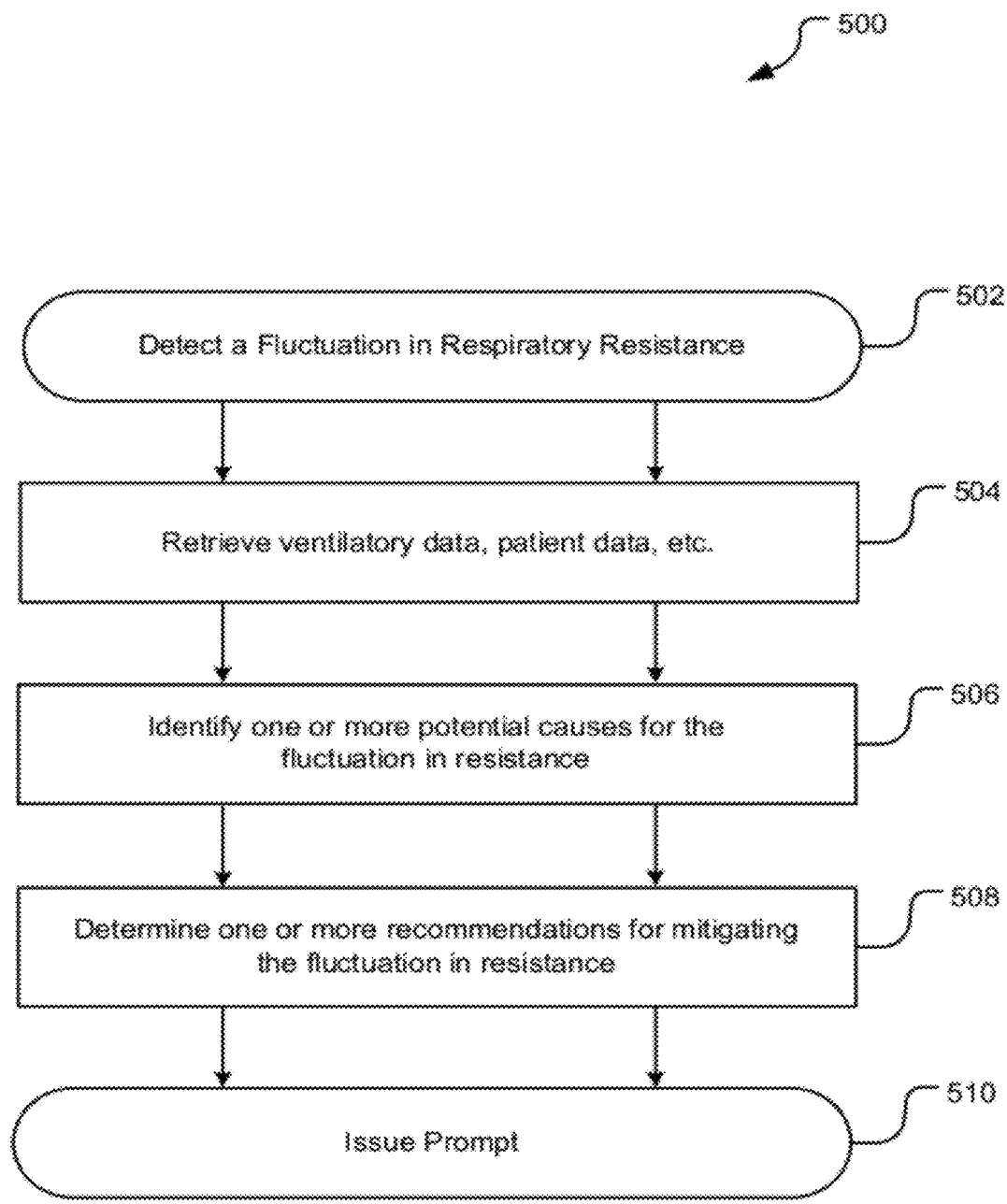
FIG. 5 is a flow chart illustrating an embodiment of a method for issuing a prompt upon determining one or more recommendations for mitigating an increase or a decrease in resistance.

FIG. 5 is a flow chart illustrating an embodiment of a method for issuing a prompt upon determining one or more recommendations for mitigating an increase or a decrease in resistance.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

Method 500 begins with detect operation 502, wherein the ventilator detects a fluctuation (either an increase or a decrease) in resistance, as described above with reference to method 300.

At retrieve operation 504, the ventilator may retrieve ventilatory data, patient data, and/or any other data, equation, protocol, standard, etc., as described with reference to operation 304.

At identify operation 506, the ventilator may identify one or more potential causes for the fluctuation in resistance, as described above with reference to method 400.

At determine operation 508, the ventilator may determine one or more recommendations for mitigating the fluctuation in resistance. According to embodiments, based on each of the one or more potential causes and the retrieved ventilatory data, patient data, etc., the ventilator may determine one or more appropriate recommendations. For example, if one of the identified potential causes for an increase in resistance is a clogged expiratory filter, the ventilator may determine an appropriate recommendation for mitigating the increased resistance includes checking and/or changing the expiratory filter. Alternatively, if one of the identified potential causes for an increase in resistance is improper patient position, the ventilator may determine an appropriate recommendation for mitigating the increased resistance includes repositioning the patient. Alternatively still, if one of the identified potential causes for an increase in resistance is bronchial constriction, the ventilator may evaluate available ventilatory data, patient data, etc., and may determine that the patient is diagnosed with asthma and that an appropriate recommendation for mitigating the increased resistance includes suggesting administration of a bronchodilator. Alternatively still, if one of the identified potential causes for an increase in resistance is an inflammatory response, the ventilator may evaluate available ventilatory data, patient data, etc., and may determine that the patient is diagnosed with ARDS and that an appropriate recommendation for mitigating the increased resistance includes suggesting bronchodilator therapy or suctioning the patient airway. Alternatively still, if one of the identified potential causes for a decrease in resistance is a leak in the ventilatory circuit, the ventilator may determine an appropriate recommendation for mitigating the decreased resistance includes suggesting checking the ventilatory circuit. As should be appreciated, any number of appropriate recommendations for mitigating a fluctuation in resistance may be determined based on a particular potential cause of the fluctuation and available ventilatory data, patient data, etc. Furthermore, according to embodiments, one or more recommendations may be determined for each of the identified one or more potential causes for a fluctuation in resistance.

At issue prompt operation 510, the ventilator may issue a prompt displaying the one or more recommendations for mitigating the fluctuation in resistance via any suitable means. For example, the recommendation may provide: "Increased Resistance Detected, Check Expiratory Filter," "Increased Resistance Detected, Consider Bronchodilator Therapy," "Increased Resistance Detected, Consider Suctioning Patient Airway," or "Decreased Resistance Detected, Suggest Checking Ventilatory Circuit for Leak," etc. As described above, the prompt may be displayed by any suitable means in any suitable location on the ventilator or a remote monitor. For example, the prompt may be displayed as a tab, banner, dialog box, or other suitable type of display, along a border of the graphical user interface, near an alarm display or bar, or in any other suitable location. The prompt may further be displayed in areas of the user interface that are either blank or that cause minimal distraction from the ventilatory data and other graphical representations provided by the GUI. The prompt may be provided in a transparent form, or otherwise, for minimizing distraction, and may be cleared upon clinician viewing.

According to some embodiments, the ventilator may display the one or more recommendations for mitigating the increase or decrease in resistance on an expanded prompt. That is, according to embodiments, the ventilator may notify the clinician of an increase or a decrease in resistance on an initial prompt. For example, the notification may display: "Increased Resistance Detected" or "Decreased Resistance Detected." The initial prompt may provide an icon or other selectable control such that upon clinician selection the one or more recommendations for mitigating the increase or decrease in resistance may be displayed on an expanded prompt. According to embodiments, the one or more recommendations for mitigating the increase or decrease in resistance may be displayed along with each of one or more potential causes (or a subset thereof) on the expanded prompt. According to alternative embodiments, only the one or more recommendations for mitigating the increase or the decrease in resistance may be displayed on the expanded prompt. According to some embodiments, a recommendation associated with a more likely potential cause may be displayed as a primary recommendation and a recommendation associated with a less likely potential cause may be displayed as a secondary recommendation. For example, the initial prompt may display "Increased Resistance Detected" or "Increased Resistance Detected, Condensate Accumulation Likely," and, upon selection of an expand icon or otherwise, the expanded prompt may display a primary recommendation of: "Consider Draining Condensate from Circuit" and a secondary recommendation of: "Consider Changing Expiratory Filter."

The expanded prompt may be provided adjacent to the initial prompt along a border of the graphical user interface, near an alarm display or bar, or in any other suitable location. The shape and size of the expanded prompt may further be optimized for easy viewing with minimal interference to other ventilatory displays. The initial prompt and/or expanded prompt may be provided in a transparent form, or otherwise, for minimizing distraction, and may be cleared upon clinician viewing.

Ventilator GUI Display of Prompt

Figure 6:
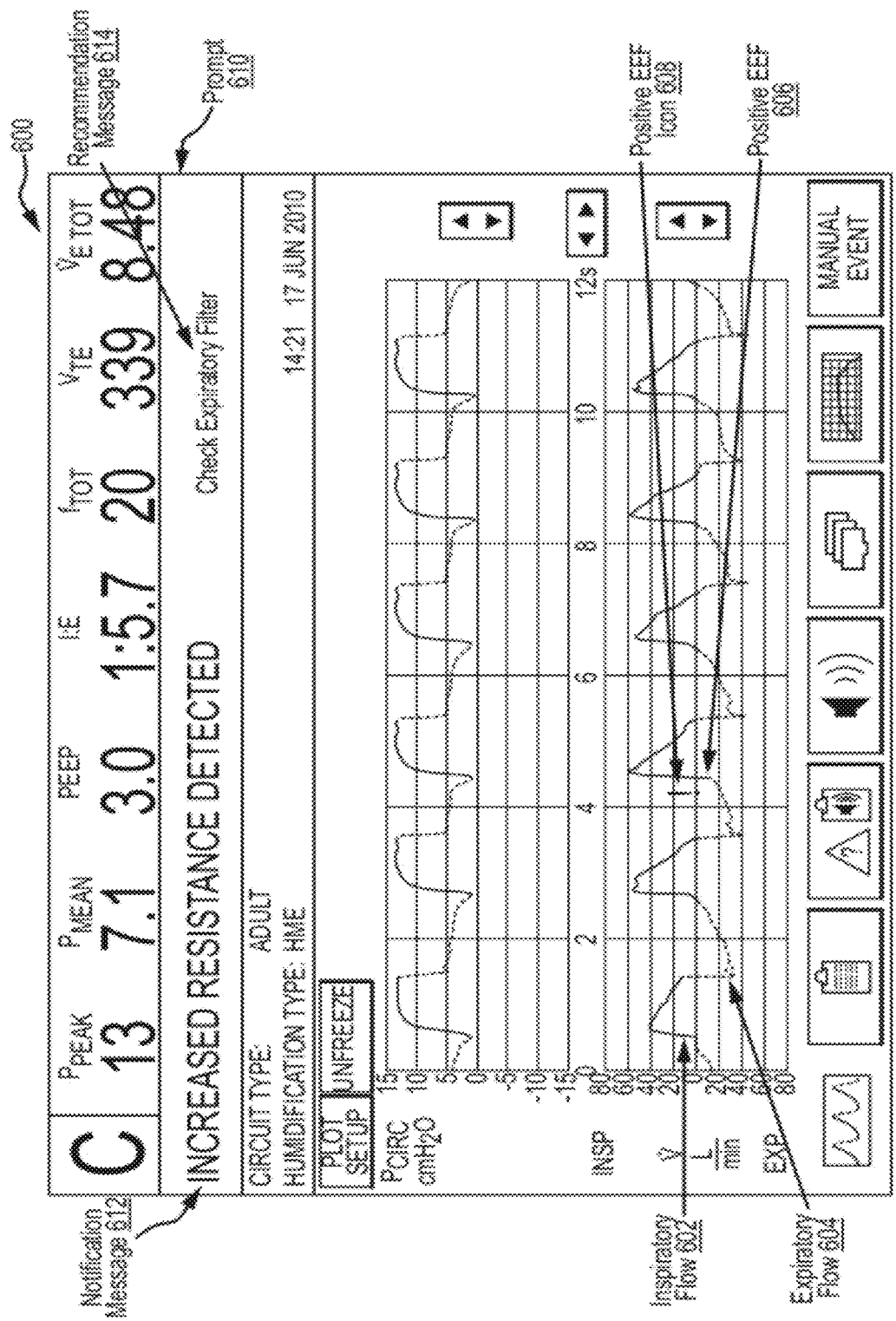
FIG. 6 is an illustration of an embodiment of a graphical user interface displaying a prompt comprising an increased resistance notification and a recommendation for mitigating the increased resistance.

FIG. 6 is an illustration of an embodiment of a graphical user interface displaying a prompt comprising an increased resistance notification and a recommendation for mitigating the increased resistance.

Graphical user interface 600 may display various monitored and/or derived data to the clinician during ventilation of a patient. In addition, graphical user interface 600 may display various messages to the clinician (e.g., alarm messages, etc.). Specifically, graphical user interface 600 may display a prompt as described herein.

According to embodiments, the ventilator may monitor and evaluate various ventilatory parameters based on one or more predetermined thresholds to detect a fluctuation in resistance. In some cases, the ventilator may determine that the fluctuation in resistance is a decrease in resistance. In other cases, the ventilator may determine that the fluctuation in resistance is an increase in resistance. For example, a detection of positive end-expiratory flow (EEF) may be indicative of an increase in resistance. As illustrated, a flow waveform may be generated and displayed by the ventilator on graphical user interface 600. As further illustrated, the flow waveform may be displayed such that inspiratory flow 602 is represented in a different color (e.g., green) than expiratory flow 604 (e.g., yellow). Although expiratory flow may preferably approximate zero at the end of expiration, in some instances EEF may not reach zero before inspiration begins, as illustrated by positive EEF 606. According to embodiments, positive EEF may be identified by a positive EEF icon 608, or other identifier, such that a clinician may readily identify positive EEF on the flow waveform. Additionally or alternatively, the flow waveform may be frozen for a period of time such that the clinician may be alerted as to the position in time of the incidence of positive EEF along the flow waveform. According to some embodiments, when positive EEF is detected, the ventilator may make a determination that resistance has increased by evaluating additional ventilatory data such as trended resistance, evaluation of PV loops, etc.

Upon a determination that resistance has increased, the graphical user interface 600 may display a prompt, e.g., prompt 610.

According to embodiments, prompt 610 may be displayed in any suitable location such that a clinician may be alerted regarding the detected increase in resistance, but while allowing other ventilatory displays and data to be visualized substantially simultaneously. As illustrated, prompt 610 is presented as a bar or banner across an upper region of the graphical user interface 600. However, as previously noted, prompt 610 may be displayed as a tab, icon, button, banner, bar, or any other suitable shape or form. Further, prompt 610 may be displayed in any suitable location within the graphical user interface 600. For example, prompt 610 may be located along any border region of the graphical user interface 600 (e.g., top, bottom, or side borders) (not shown), across an upper region (shown), or in any other suitable location. Further, as described herein, prompt 610 may be partially transparent (not shown) such that ventilatory displays and data may be at least partially visible behind prompt 610.

Specifically, prompt 610 may alert the clinician that increased resistance has been detected, for example by notification message 612. As described herein, notification message 612 may alert the clinician of an increase in resistance via any suitable means, e.g., "Increased Resistance Detected." Prompt 610 may further include information regarding one or more potential causes for the increased resistance. For example, if the ventilator determined that the increased resistance was likely caused by a clogged expiratory filter, this information may be provided to the clinician (e.g., "Increased Resistance Detected, Expiratory Filter Likely Clogged") (not shown). Prompt 610 may further include information regarding one or more recommendations for mitigating the increased resistance. With reference to the above example, if the ventilator determined that the increased resistance was likely caused by a clogged expiratory filter, the ventilator may provide a recommendation to the clinician (e.g., "Increased Resistance Detected, Check Expiratory Filter") (shown). According to the illustrated embodiment, recommendation message 614 is provided along with the notification message 612 in a banner. According to alternative embodiments, the notification message 612 alone may be provided on an initial prompt (not shown).

As may be appreciated, the disclosed data, graphics, and smart prompt illustrated in graphical user interface 600 may be arranged in any suitable order or configuration such that information and alerts may be communicated to the clinician in an efficient and orderly manner. The disclosed data, graphics, and smart prompt are not to be understood as an exclusive array, as any number of similar suitable elements may be displayed for the clinician within the spirit of the present disclosure. Further, the disclosed data, graphics, and smart prompt are not to be understood as a necessary array, as any number of the disclosed elements may be appropriately replaced by other suitable elements without departing from the spirit of the present disclosure. The illustrated embodiment of the graphical user interface 600 is provided as an example only, including potentially useful information and alerts that may be provided to the clinician to facilitate communication of the detected fluctuation in resistance in an orderly and informative way, as described herein.

Figure 7:
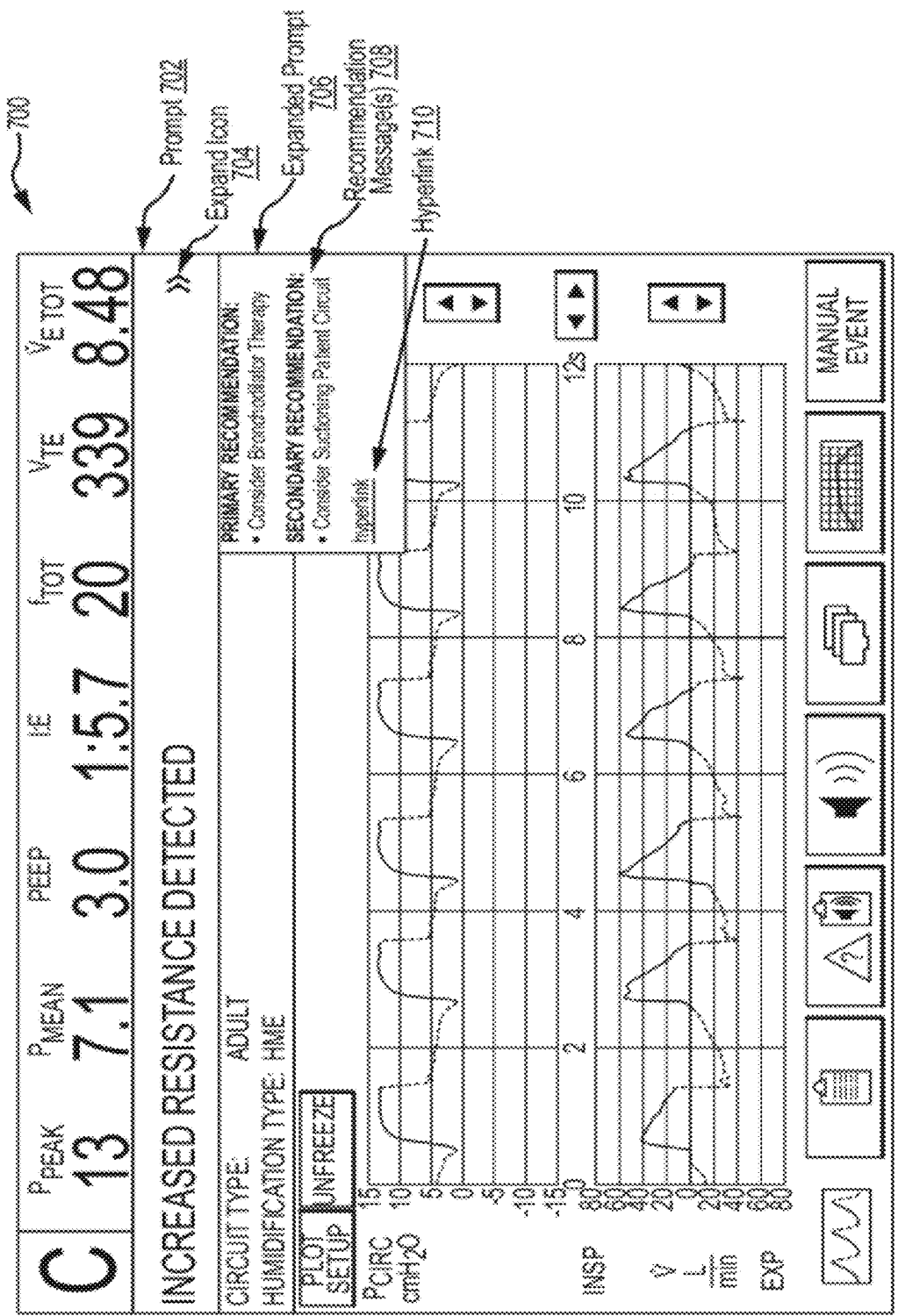
FIG. 7 is an illustration of an embodiment of a graphical user interface displaying a prompt comprising an increased resistance notification and an expanded prompt comprising one or more recommendations for mitigating the increase in resistance during ventilation of a patient.

FIG. 7 is an illustration of an embodiment of a graphical user interface displaying a prompt comprising an increased resistance notification and an expanded prompt comprising one or more recommendations for mitigating the increase in resistance during ventilation of a patient.

Graphical user interface 700 may display various monitored and/or derived data to the clinician during ventilation of a patient, as described with reference to graphical user interface 600.

According to embodiments, the ventilator may monitor and evaluate various ventilatory parameters based on one or more predetermined thresholds to detect a fluctuation in resistance. In some cases, the ventilator may determine that the fluctuation in resistance is a decrease in resistance. In other cases, the ventilator may determine that the fluctuation in resistance is an increase in resistance. For example, a detection of positive end-expiratory flow (EEF) may be indicative of an increase in resistance. However, according to some embodiments, when positive EEF is detected, the ventilator may make a determination that resistance has increased by evaluating additional ventilatory data such as trended resistance, evaluation of PV loops, evaluation of ventilator setup data, etc. Upon a determination that resistance has increased, the graphical user interface 700 may display a prompt, e.g., prompt 702.

According to embodiments, prompt 702 may be displayed in any suitable location such that a clinician may be alerted regarding the detected increase in resistance, but while allowing other ventilatory displays and data to be visualized substantially simultaneously, as described above with reference to prompt 610.

Specifically, prompt 702 may alert the clinician that increased resistance has been detected, for example by a notification message (e.g., "Increased Resistance Detected").

According to embodiments, prompt 702 may be expanded to provide additional information and/or recommendations to the clinician regarding the detected fluctuation in resistance (e.g., increase in resistance). For example, an expand icon 704 may be provided within a suitable area of the prompt 702. According to embodiments, upon selection of the expand icon 704 via any suitable means, the clinician may optionally expand prompt 702 to acquire additional information and/or recommendations for mitigating the detected increase in resistance, e.g. expanded prompt 706. As described above for prompt 610, expanded prompt 706 may be displayed as a tab, icon, button, banner, bar, or any other suitable shape or form.

Further, expanded prompt 706 may be displayed in any suitable location within the graphical user interface 700. For example, expanded prompt 706 may be displayed below (shown) prompt 702, to a side (not shown) of prompt 702, or otherwise logically associated with prompt 702. According to other embodiments, an initial prompt may be hidden (not shown) upon displaying expanded prompt 706. Expanded prompt 706 may also be partially transparent (not shown) such that ventilatory displays and data may be at least partially visible behind expanded prompt 706.

According to embodiments, expanded prompt 706 may comprise additional information (not shown) and/or one or more recommendation messages 708 regarding a detected fluctuation in resistance (e.g., an increase in resistance). For example, the one or more recommendation messages 708 may include one or more primary recommendation messages and one or more secondary recommendation messages. According to embodiments, the one or more primary recommendation messages may provide one or more suggestions for mitigating the increase in resistance based on more likely potential causes for the increase in resistance. The one or more secondary recommendation messages may provide one or more suggestions for mitigating the increase in resistance based on less likely potential causes for the increase in resistance. For example, if an increase in resistance was likely caused by inflammation of the airways and the patient was diagnosed with ARDS, a primary recommendation message may include: "Consider Bronchodilator Therapy." Additionally, according to embodiments, a secondary recommendation message may include: "Consider Suctioning Patient Airway."

According to embodiments, expanded prompt 706 may also include one or more hyperlinks 710, which may provide immediate access to the display and/or settings screens associated with a detected fluctuation in resistance. For example, associated parameter settings screens may be accessed from expanded prompt 706 via hyperlink 710 such that the clinician may address the detected fluctuation in resistance by adjusting one or more parameter settings as necessary. Alternatively, associated parameter display screens may be accessed such that the clinician may view clinical data associated with the detected fluctuation in resistance in the form of charts, graphs, or otherwise. That is, according to embodiments, the clinician may access the ventilatory data that implicated the detected fluctuation in resistance for verification purposes.

As may be appreciated, the disclosed data, graphics, and smart prompt illustrated in graphical user interface 700 may be arranged in any suitable order or configuration such that information and alerts may be communicated to the clinician in an efficient and orderly manner. The disclosed data, graphics, and smart prompt are not to be understood as an exclusive array, as any number of similar suitable elements may be displayed for the clinician within the spirit of the present disclosure. Further, the disclosed data, graphics, and smart prompt are not to be understood as a necessary array, as any number of the disclosed elements may be appropriately replaced by other suitable elements without departing from the spirit of the present disclosure. The illustrated embodiment of the graphical user interface 700 is provided as an example only, including potentially useful information and alerts that may be provided to the clinician to facilitate communication of the detected fluctuation in resistance in an orderly and informative way, as described herein.

Figure 8:
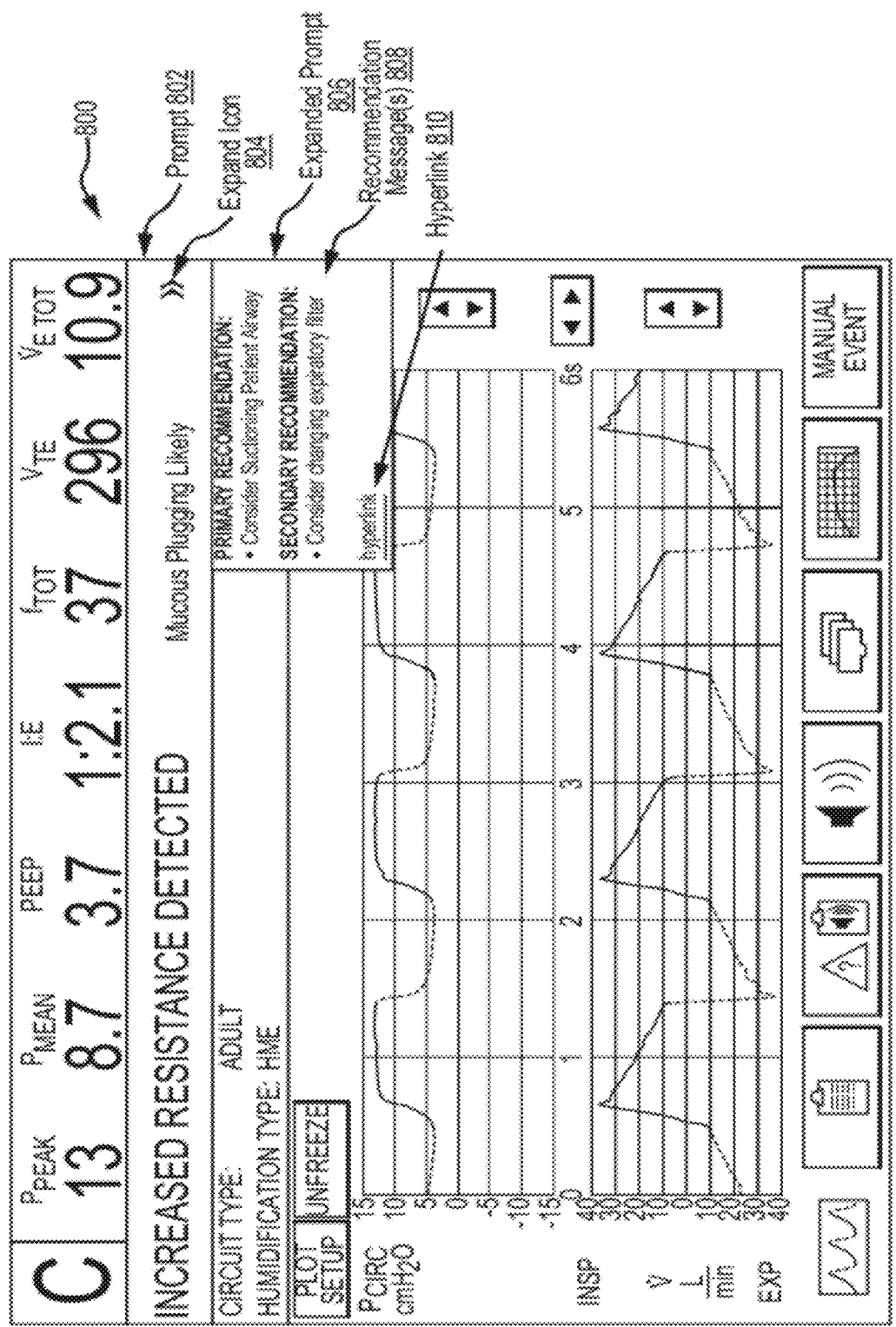
FIG. 8 is an illustration of an embodiment of a graphical user interface displaying a prompt comprising an increased resistance notification and a potential cause notification and an expanded prompt comprising one or more recommendations for mitigating the increased resistance during ventilation of a patient.

FIG. 8 is an illustration of an embodiment of a graphical user interface displaying a prompt comprising an increased resistance notification and a potential cause notification and an expanded prompt comprising one or more recommendations for mitigating the increased resistance during ventilation of a patient.

As described above with reference to FIG. 7, graphical user interface 800 may display various monitored and/or derived data to the clinician during ventilation of a patient. In addition, graphical user interface 800 may display a prompt 802 including a notification message regarding a detected fluctuation in resistance, e.g., "Increased Resistance Detected" (shown) or "Decreased Resistance Detected" (not shown). According to some embodiments, one or more potential causes for the fluctuation in resistance may be displayed on prompt 802, e.g., "Mucous Plugging Likely" (shown), "Bronchospasm Likely" (not shown), "Expiratory Filter Likely Clogged" (not shown), etc. According to embodiments, only a most likely potential cause may be displayed on prompt 802. According to alternative embodiments, one or more potential causes for a fluctuation in resistance may be determined by the ventilator, but may not be displayed to the clinician.

According to embodiments, as described above, an expand icon 804 may be provided within a suitable area of prompt 802. Upon selection of the expand icon 804, the clinician may optionally expand prompt 802 to acquire additional information and/or recommendations for mitigating a fluctuation in resistance. For example, expanded prompt 806 may be provided upon selection of expand icon 804. As described above for prompts 610 and 706, expanded prompt 806 may be displayed in any suitable shape or form in any suitable location within the graphical user interface 800.

According to embodiments, expanded prompt 806 may comprise additional information (not shown) and/or one or more recommendation messages 808 regarding a detected fluctuation in resistance (e.g., an increase in resistance). For example, the one or more recommendation messages 808 may include one or more primary recommendation messages and one or more secondary recommendation messages. According to embodiments, the one or more primary recommendation messages may provide one or more suggestions for mitigating the increase in resistance based on more likely potential causes for the increase in resistance. For example, if the ventilator determined that mucous plugging is a likely cause for the increase in resistance, a primary recommendation message may provide: "Consider Suctioning Patient Airway" (shown). The one or more secondary recommendation messages may provide one or more suggestions for mitigating the increase in resistance based on less likely potential causes for the increase in resistance. For example, if the ventilator determined that a clogged expiratory filter is a less likely cause for the increase in resistance, a secondary recommendation message may provide: "Consider Changing Expiratory Filter" (shown).

As described above, according to embodiments, expanded prompt 806 may also include one or more hyperlinks 810, which may provide immediate access to the display and/or settings screens associated with the detected fluctuation in resistance. For example, associated parameter settings screens may be accessed from expanded prompt 806 via hyperlink 810 such that the clinician may address the detected fluctuation in resistance by adjusting one or more parameter settings as necessary. Alternatively, associated parameter display screens may be accessed such that the clinician may view clinical data associated with the detected fluctuation in resistance in the form of charts, graphs, or otherwise.

As may be appreciated, the disclosed prompt and recommendation messages illustrated in graphical user interface 800 may be arranged in any suitable order or configuration such that information and alerts may be communicated to the clinician in an efficient and orderly manner. Indeed, the illustrated embodiment of the graphical user interface 800 is provided as an example only, including potentially useful information and recommendations that may be provided to the clinician to facilitate communication of suggestions for mitigating the detected fluctuation in resistance in an orderly and informative way, as described herein.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A ventilator-implemented method for issuing a prompt in response to detecting a fluctuation in resistance during ventilation of a patient, the method comprising:
    retrieving ventilatory data;
    identifying a maximum threshold and a minimum threshold for resistance;
    trending resistance during ventilation of the patient;
    detecting a fluctuation in resistance when the trended resistance breaches one of the maximum threshold and the minimum threshold; and
    displaying a notification regarding detection of the fluctuation in resistance.

2. The method of claim 1, further comprising retrieving patient data, wherein the patient data comprises at least one of: a patient diagnosis, a patient predicted body weight (PBW), and a patent gender.

3. The method of claim 2, further comprising:
    determining one or more potential causes for the fluctuation in resistance based at least in part on the retrieved patient data.

4. The method of claim 3, further comprising:
    determining one or more recommendations for mitigating the fluctuation in resistance based on the determined one or more potential causes and at least some patient data; and
    displaying the one or more recommendations.

5. The method of claim 1, further comprising:
    determining one or more potential causes for the fluctuation in resistance based at least in part on the retrieved ventilatory data.

6. The method of claim 5, further comprising:
    determining one or more recommendations for mitigating the fluctuation in resistance based on the determined one or more potential causes and at least some ventilatory data; and
    displaying the one or more recommendations.

7. The method of claim 6, wherein displaying further comprises:
    displaying an icon for accessing the one or more recommendations, wherein upon activating the icon the one or more recommendations are displayed.

8. The method of claim 6, further comprising:
    displaying the notification regarding detection of the fluctuation in resistance on an expandable prompt; and
    displaying an icon for expanding the prompt to display one or more of: the one or more potential causes for the fluctuation in resistance and the one or more recommendations for mitigating the fluctuation in resistance.

9. A ventilatory system for issuing a prompt in response to detecting a fluctuation in resistance during ventilation of a patient, comprising:
    at least one processor; and
    at least one memory, communicatively coupled to the at least one processor and containing instructions that, when executed by the at least one processor, cause a controller to:
    retrieve ventilatory data;
    identify a maximum threshold and a minimum threshold for resistance;
    trend resistance during ventilation of the patient;
    detect a fluctuation in resistance when the trended resistance breaches one of the maximum threshold and the minimum threshold; and
    display a notification regarding detection of the fluctuation in resistance.

10. The ventilatory system of claim 9, further causing the controller to:
    determine one or more potential causes for the fluctuation in resistance based at least in part on the retrieved ventilatory data.

11. The ventilatory system of claim 10, further causing the controller to:
    determine one or more recommendations for mitigating the fluctuation in resistance based on the determined one or more potential causes and at least some ventilatory data; and
    display the one or more recommendations.

12. The ventilatory system of claim 11, wherein the display step further comprises:
    display an icon for accessing the one or more recommendations, wherein upon activating the icon the one or more recommendations are displayed.

13. The ventilatory system of claim 10, wherein the display step further comprises:
    display an icon for accessing the one or more potential causes, wherein upon activating the icon the one or more potential causes are displayed.

14. A graphical user interface for displaying one or more prompts in response to detecting a fluctuation in resistance, the ventilator configured with a computer having a user interface including the graphical user interface, the graphical user interface comprising:
    at least one window; and
    one or more elements within the at least one window comprising at least one prompt element for communicating information regarding detection of a fluctuation in resistance, wherein the at least one prompt element displays a notification regarding the fluctuation in resistance; and wherein detecting the fluctuation in resistance comprises trending resistance during ventilation of a patient and detecting that the trended resistance breaches one of a maximum threshold and a minimum threshold.

15. The graphical user interface of claim 14, wherein the at least one prompt element displays one or more potential causes for the fluctuation in resistance.

16. The graphical user interface of claim 14, wherein the at least one prompt element displays one or more recommendations for mitigating the fluctuation in resistance.

17. The graphical user interface of claim 14, wherein the at least one prompt element is an expandable prompt element, the expandable prompt element further comprising:
   a selectable icon, wherein upon selection the expandable prompt element displays one or more potential causes for the fluctuation in resistance.

18. The graphical user interface of claim 14, wherein the at least one prompt element is an expandable prompt element, the expandable prompt element further comprising:
   a selectable icon, wherein upon selection the expandable prompt element displays one or more recommendations for mitigating the fluctuation in resistance.

19. A ventilator processing interface for displaying one or more prompts in response to detecting a fluctuation in resistance, comprising:
   means for retrieving at least some ventilatory data;
   means for determining the fluctuation in resistance, wherein determining the fluctuation in resistance comprises trending resistance during ventilation of a patient and detecting that the trended resistance breaches one of a maximum threshold and a minimum threshold; and
   means for displaying a prompt comprising a notification of the fluctuation in resistance.

20. The ventilator processing interface of claim 19, wherein the prompt further comprises one or more recommendations for mitigating the fluctuation in resistance.

\* \* \* \* \*